US012644901B2

(12) United States Patent
Nicolajsen et al.

(10) Patent No.: US 12,644,901 B2
(45) Date of Patent: Jun. 2, 2026

(54) SENSOR DEVICE

(71) Applicant: RADIOMETER MEDICAL APS, Brønshøj (DK)

(72) Inventors: Erik Helleso Nicolajsen, Brønshøj (DK); Flemming Aas, Brønshøj (DK); Ole Hedevang Jensen, Brønshøj (DK); Cyril Nedaud, Brønshøj (DK)

(73) Assignee: RADIOMETER MEDICAL ApS, Brønshøj (DK)

( * ) Notice: Subject to any disclaimer, the term of this patent is extended or adjusted under 35 U.S.C. 154(b) by 332 days.

(21) Appl. No.: 17/621,462

(22) PCT Filed: Jul. 6, 2020

(86) PCT No.: PCT/EP2020/069004
§ 371 (c)(1),
(2) Date: Dec. 21, 2021

(87) PCT Pub. No.: WO2021/005005
PCT Pub. Date: Jan. 14, 2021

(65) Prior Publication Data
US 2022/0357355 A1 Nov. 10, 2022

(30) Foreign Application Priority Data

Jul. 5, 2019 (DK) ............................ PA 2019 00835

(51) Int. Cl.
*G01N 35/10* (2006.01)
*G01N 33/49* (2006.01)

(52) U.S. Cl.
CPC ..... *G01N 35/1095* (2013.01); *G01N 33/4915* (2013.01); *G01N 33/492* (2013.01)

(58) Field of Classification Search
CPC ........... G01N 35/1095; G01N 33/4915; G01N 33/492; G01N 2035/00356; G01N 35/08; G01N 33/487
See application file for complete search history.

(56) References Cited

U.S. PATENT DOCUMENTS 3,884,640 A 5/1975 Lock et al.
5,916,425 A 6/1999 Leader et al.
(Continued)

FOREIGN PATENT DOCUMENTS

CN 101715556 A 5/2010
CN 102262138 A 11/2011
(Continued)

OTHER PUBLICATIONS

Nie, Jinquan, Yulong Zhao, and Niancai Peng. "Multichannel oscillatory-flow PCR micro-fluidic chip with controllable temperature gradient." Microsystem Technologies 21 (2015): 41-48. (Year: 2014).*
(Continued)

*Primary Examiner* — Robert J Eom
(74) *Attorney, Agent, or Firm* — FBT Gibbons LLP

(57) ABSTRACT

The present disclosure relates to a sensor device, comprising: a measurement chamber having at least a first wall, the measurement chamber including a plurality of analyte sensors; wherein the measurement chamber allows a fluid to be analyzed to interact with each of the plurality of analyte sensors when the fluid is accommodated within the measurement chamber; the measurement chamber having an inlet configured to receive the fluid to be analyzed and an outlet configured to allow the fluid to exit the measurement chamber after having interacted with the plurality of analyte sensors; the measurement chamber defining a sample volume for accommodating the fluid to be analyzed, the sample volume extending at least between the inlet and the outlet;
(Continued)

a heating element configured to heat the fluid accommodated within the measurement chamber.

28 Claims, 9 Drawing Sheets

(56)                 References Cited

U.S. PATENT DOCUMENTS

| | | | |
|---|---|---|---|
| 8,728,288 | B2 | 5/2014 | Aas et al. |
| 2002/0079219 | A1 | 6/2002 | Zhao et al. |
| 2013/0068754 | A1* | 3/2013 | Ptasienski ................ H05B 3/28 |
| | | | 219/541 |
| 2016/0238583 | A1 | 8/2016 | Kodzius et al. |
| 2019/0008003 | A1 | 1/2019 | Samproni |
| 2019/0011429 | A1* | 1/2019 | Taagaard ............. G01N 33/492 |
| 2019/0346398 | A1* | 11/2019 | Aas .................... G01N 27/3274 |

FOREIGN PATENT DOCUMENTS

| | | | |
|---|---|---|---|
| DE | 102 03 211 | A1 | 8/2003 |
| EP | 1 362 827 | A1 | 11/2003 |
| JP | 2005/201893 | A | 7/2005 |
| JP | 2008/296119 | A | 5/2007 |
| WO | WO 94/19683 | A1 | 9/1994 |
| WO | WO 2016/096725 | A1 | 6/2016 |
| WO | WO 2016/097078 | A1 | 6/2016 |
| WO | WO 2017/019569 | A1 | 2/2017 |
| WO | WO 2018/104134 | A1 | 6/2018 |

OTHER PUBLICATIONS

Selva, Bertrand, Julien Marchalot, and Marie-Caroline Jullien. "An optimized resistor pattern for temperature gradient control in microfluidics." Journal of Micromechanics and Microengineering 19.6 (2009): 065002. (Year: 2009).*

Shameli, Seyed Mostafa, et al. "Bilinear temperature gradient focusing in a hybrid PDMS/glass microfluidic chip integrated with planar heaters for generating temperature gradients." Analytical chemistry 84.6 (2012): 2968-2973. (Year: 2012).*

International Search Report for International Application No. PCT/EP2020/069004, dated Dec. 11, 2020 (three pages).

Written Opinion of the International Search Authority for International Application No. PCT/EP2020/069004.

Chinese First Office Action for CN Patent Application No. 202080049265.

Chinese Rejection Decision for CN Patent Application No. 202080049265.4.

Japanese Decision to Grant for JP Patent Application No. 2022500526.

Japanese Notification of Reasons for Rejection for JP Patent Application No. 2024-129937.

* cited by examiner

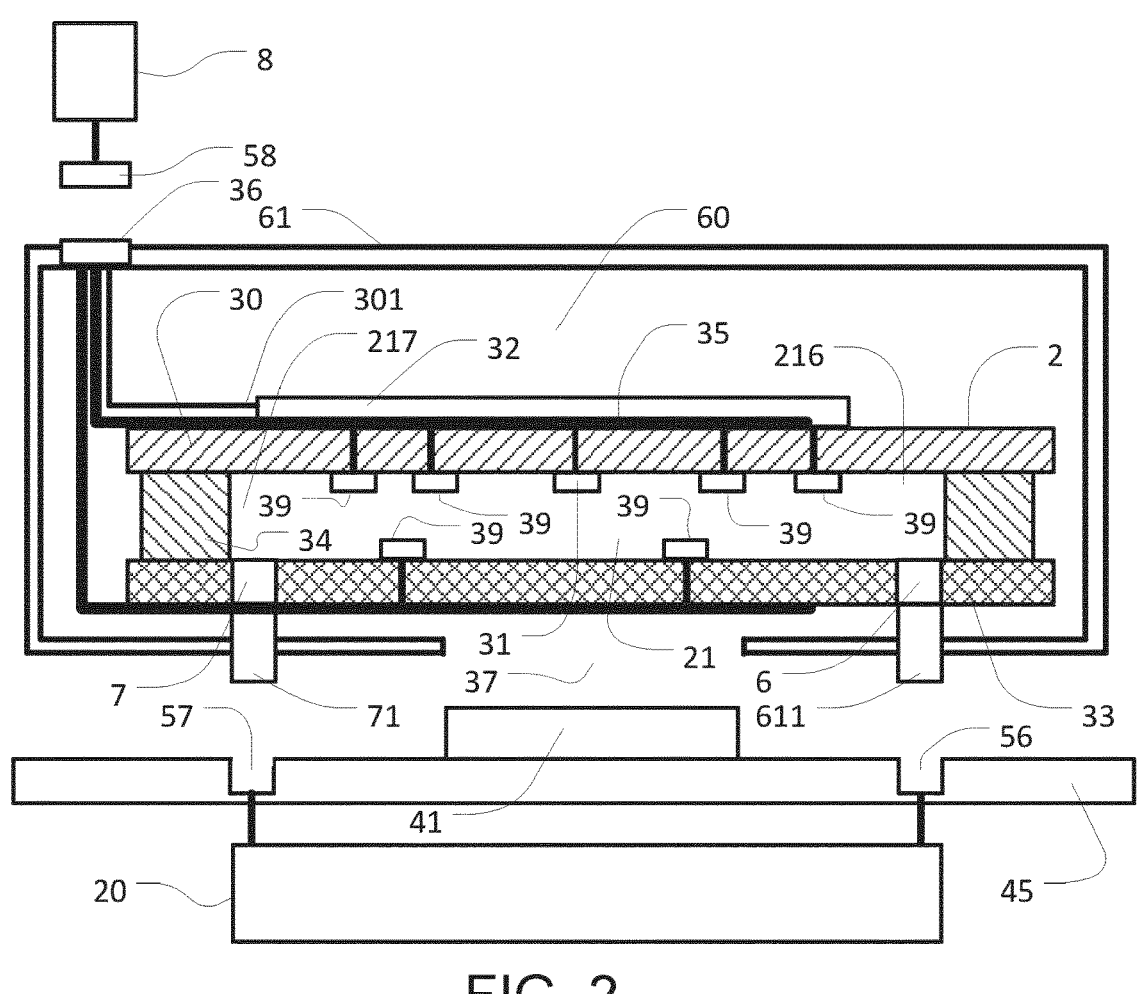
FIG. 2
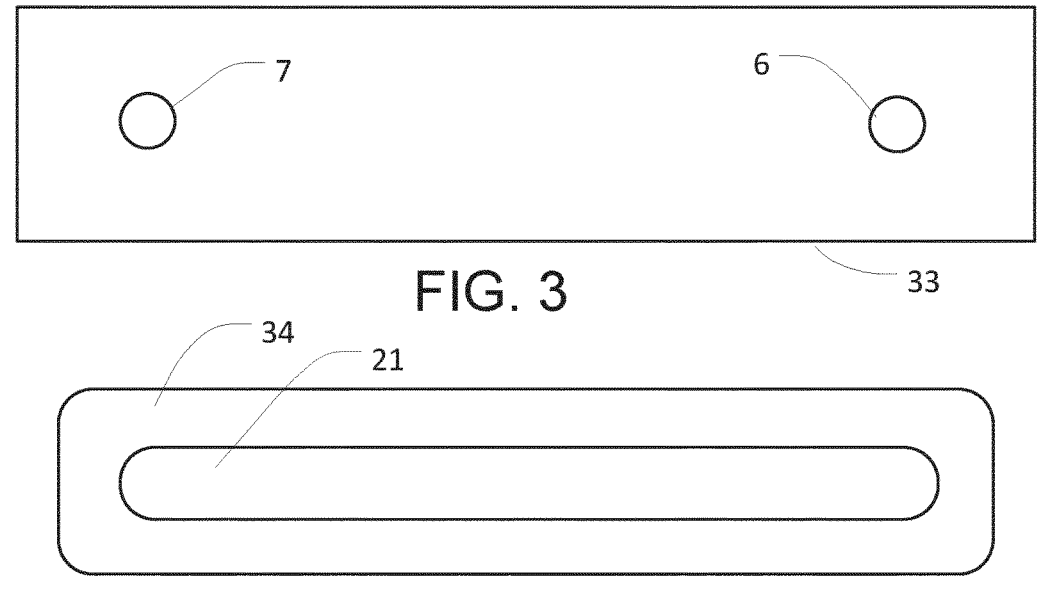
FIG. 3
FIG. 4

SENSOR DEVICE

This application is a national stage filing under 35 U.S.C. § 371 of International Application No. PCT/EP2020/069004, filed on Jul. 6, 2020, which claims priority of Danish Patent Application No. PA 2019 00835, filed on Jul. 5, 2019. The contents of these applications are each incorporated herein by reference.

TECHNICAL FIELD

The present invention relates to a sensor device and to an analyzer apparatus comprising such a sensor device.

BACKGROUND OF THE INVENTION

Analyzers for measuring physical parameters of analytes in a fluid sample by means of respective analyte sensors are widely used in various industries, such as food industry, environmental industry, as well as medical and clinical industry.

Such analyzers often comprise a sensor device having a measurement chamber for accommodating the sample to be analyzed. Measurement chambers may have multiple analyte sensors distributed throughout the measurement chamber.

To ensure accurate and precise results, the performance of such sensor devices requires a sufficiently accurate temperature control of the samples to be analyzed.

To this end, known sensor devices comprise heating elements.

An example of a sensor device comprising a heating element is disclosed in WO2017120464.

It is generally desirable to maintain production costs of sensor devices low or to even reduce production costs. This is particularly desirable because the sensor devices often have a limited lifetime and are provided as replaceable parts.

Nevertheless, it is important that the sensor device provides accurate, precise and reliable measurement results. As the operation of many sensors is sensitive to the sample temperature, it is therefore desirable to maintain a uniform temperature throughout a measurement chamber that has multiple analyte sensors distributed across the measurement chamber.

The accurate and precise operation of analyzer systems is of particular importance in clinical analysis applications for analyzing physical parameters of analytes in bodily fluids, such as whole blood. In addition to the accuracy, precision, and reliability requirements, such analyzer systems for clinical applications are also subject to further critical constraints, such as a short analysis time i.e. short time from application of the sample to obtaining a measurement result, and the capability of providing the highly reliable results from very small sample volumes.

A combination of all these constraints is particularly relevant in blood analyzers. Blood analyzers provide measurements of various parameters for analyzing the blood of a mammal subject, e.g. for establishing and/or monitoring a biological condition of the subject. Typically, the mammal subject is a human patient. In a variety of instances it is desirable to measure e.g. the partial pressure of blood gasses in a whole blood sample of the mammal subject, concentrations of electrolytes and metabolites in the blood sample, as well as the hematocrit value of the blood sample. For example, measuring $pCO_2$, $pO_2$, pH, $Na^+$, $K^+$, $Ca^{2+}$, $Cl^-$, $Mg^{2+}$, glucose, lactate, creatinine, urea and hemoglobin and hemoglobin-derivate values are primary clinical indications in assessing the condition of a medical patient. A number of different analyzers currently exist for making such measurements.

In order to use as little of the patient's blood as possible in each analysis performed, it is desirable to provide a relatively small measuring chamber which accommodates the sample to be analyzed and to provide multiple analyte sensors in order to be able to ascertain multiple measurements using the same sample. Performing blood analysis using a small blood sample is important when a relatively large number of samples must be taken in a relatively short amount of time or if the volume of blood is limited, as e.g. in neonates. For example, patients in intensive care may require a sampling frequency of as many as 15-20 samples per day for blood gas and clinical chemistry measurements, leading to a potentially large loss of blood during patient assessment. Furthermore, in order to limit the number of tests which must be performed it is desirable to gather as much information as possible upon completion of each test. Furthermore, for the same reasons, it is important that the measurements and corresponding analysis results obtained from these measurements are reliable. In clinical environments it is also important that the time required for analyzing the individual samples is as short as possible because critical clinical decisions may depend on the knowledge of the measurement results. Moreover, an efficient use of analyzers is facilitated if the analyzers can be operated with a high throughput.

It thus remains desirable to provide improved sensor devices that fulfil one or more of the above objectives or at least provide suitable alternatives to known sensor devices.

SUMMARY OF THE INVENTION

According to a first aspect, disclosed herein are embodiments of a sensor device, comprising:
- a measurement chamber having at least a first wall, the measurement chamber including a plurality of analyte sensors; wherein the measurement chamber allows a fluid to be analyzed to interact with each of the plurality of analyte sensors when the fluid is accommodated within the measurement chamber; the measurement chamber having an inlet configured to receive the fluid to be analyzed and an outlet configured to allow the fluid to exit the measurement chamber after having interacted with the plurality of analyte sensors; the measurement chamber defining a sample volume for accommodating the fluid to be analyzed, the sample volume extending at least between the inlet and the outlet; and
- a heating element configured to heat the fluid accommodated within the measurement chamber, wherein the heating element is configured to provide a larger heating effect in a proximity of the inlet of the measurement chamber than in a proximity of the outlet of the measurement chamber.

It has turned out that the provision of a heating element that is configured to provide a larger heating effect in a proximity of the inlet of the measurement chamber than in a proximity of the outlet of the measurement chamber provides a more uniform temperature distribution across the plurality of analyte sensors, thereby facilitating accurate and precise measurements for all analyte sensors while maintaining relatively low production costs and short measurement cycle times. In particular, embodiments of the sensor device described herein provide a uniform sample temperature across the entire measurement chamber, or at least along the flow path of the sample fluid between the inlet and the outlet. Moreover, some embodiments of the invention provide increased uniformity in sample temperature per heating element. Thereby, similar uniformity in temperature in the measurement chamber can be achieved with a smaller number of heating elements. This in turn reduces manufacturing complexity and costs.

The heating effect provided by a portion of the heating element may be defined by the heating effect provided throughout one measurement cycle, i.e. from when the sample begins to enter the measurement chamber through the inlet until the sample has left the measurement chamber through the outlet. To this end, the heating element may be configured to provide a larger heating power, i.e. a larger heating effect per unit time, in a proximity of the inlet of the measurement chamber than in a proximity of the outlet of the measurement chamber.

The measuring results of the sensor device responsive to interaction of the fluid with the analyte sensors are typically temperature dependent. Accurate and reliable measurement results thus often require the fluid to have a predetermined temperature. For example, for body fluids, the temperature at which the measurements are to be performed is typically specified to a range corresponding to body temperature, such as between 35° C. and 40° C., between 36° C. and 39° C., between 36° C. and 38° C. or about 37° C. However, other target temperatures may be used in other embodiments.

In some embodiments, the sample temperature of the fluid when entering the measurement chamber is lower than a target temperature at which the measurement is to be performed. Moreover, the initial temperature of the fluid sample when being inserted into the analyzer may vary. For example, fluid samples may have different room temperatures when inserted into an analyzer or they may be refrigerated. Even in embodiments where the fluid is pre-heated by the analyzer before entering the measurement chamber, the sample temperature of the fluid when entering the measurement chamber is often still lower than the target temperature.

The analyte sensors may be located at respective positions, distributed across the measurement chamber, e.g. across the entire measurement chamber or only across a portion of the measurement chamber. In some embodiments, the temperature of the fluid inside the measurement chamber should be as uniform as possible across the measurement chamber, at least across the portion of the measurement chamber where the analyte sensors are located. The inventors have realized that a non-uniform distribution of the heating effect results in a more uniform temperature distribution of the fluid across the measurement chamber, in particular along the flow path defined between the inlet and the outlet. In particular, providing a higher heating effect in a proximity of the inlet than in a proximity of the outlet helps to avoid overheating of the sample once it approaches the outlet. Providing a non-uniform heating effect allows interaction of a sample with multiple analyte sensors at a uniform sample temperature while avoiding extended processing times due to e.g. obtaining thermal equilibrium or extended pre-heating of the sample and/or the measurement chamber.

The measurement chamber may have various shapes and sizes, e.g. cylindrical, box shaped or the like. The measurement chamber may be an elongated chamber having an inlet end where the inlet is located and an outlet end where the outlet is located. Generally, at least during filling and emptying of the measurement chamber, the sample flows in a direction from the inlet towards the outlet. The measurement chamber defines a flow path between the inlet and the outlet of the measurement chamber. The flow path has a length defined between the inlet and the outlet. In some embodiments, the length of the flow path is larger than the dimension(s) of the measurement chamber in one or both other directions, across the flow path, i.e. larger than a width and/or a height of the measurement chamber. For example, the measurement chamber may have cross-sectional dimensions in the millimeter and/or sub-millimeter range.

The measurement chamber defines a sample volume which may be defined by one or more walls of the measurement chamber. For example, the measurement chamber may be defined by an ellipsoid-shaped wall. In other examples the measurement chamber may be a cylindrical chamber where the first wall is a tubular wall. In other embodiments the sensor device comprises at least a second wall of the measurement chamber opposite the first wall. For example the first and second walls may be planar or curved walls and the measurement chamber may be defined between the first and second walls. The flow path between the inlet and the outlet may be linear, curved, meandering and/or have a different shape. The heating element is configured to provide a larger heating effect along a first portion of the flow path, proximal to the inlet, and a smaller heating effect along a second portion of the flow path, downstream of the first portion and proximal to the outlet. In some embodiments the heating element is configured to only provide a heating effect along the first portion and substantially no heating effect along the second portion of the flow path.

Generally, the measurement chamber may have a uniform width and/or height along the flow path. Alternatively, the measurement chamber may have a non-uniform width and/or a non-uniform height along the flow path. For example, the measurement chamber may have one or more broadenings or narrowing's, e.g. around the analyte sensors.

Similarly, the analyte sensors may be attached to or integrated into one or more of the walls of the measurement chamber. For example, the analyte sensors may include material deposited on a wall of the measurement chamber, by a sensor attached to or integrated into the wall, and/or the like.

When the heating element is positioned at one or more of the walls of the measurement chamber, a rapid, reliable, and reproducible conditioning of the fluid sample to a desired target temperature may be achieved, where analysis measurements can be performed. To this end, the heating element may be physically attached to or integrated with one or more of the walls of the measurement chamber. By physically attaching at least one heating element to at least one wall of the measurement chamber or by integrating at least one heating element with at least one wall of the measurement chamber, good thermal transfer between the heating element and the fluid sample inside the measurement chamber may be achieved so as to ensure a rapid and reproducible transfer of heating energy from the heating element to the fluid sample. While thermal losses are unavoidable, physical attachment of the heating element to, or integration of the heating element with at least one wall of the measurement chamber provides a well-controlled heating mechanism, where the heat transferred to the sample is systematically linked to the heat generated by the heating element, and further to the power/energy consumed by the heating element. The heating element may be attached or integrated to the wall in various ways, e.g. printed, bonded, glued or the like. The heating element may be disposed at more than one wall, e.g. at both the first and the second wall or at both the first and the second and at least one of any further walls. Alternatively, the heating element may be disposed only at the first wall.

Generally, according to a second aspect, disclosed herein are embodiments of a sensor device, comprising:

a measurement chamber having at least a first wall and a second wall, opposite the first wall, the measurement chamber including a plurality of analyte sensors; wherein the measurement chamber allows a fluid to be analyzed to interact with each of the plurality of analyte sensors when the fluid is accommodated within the measurement chamber; the measurement chamber having an inlet configured to receive the fluid to be analyzed and an outlet configured to allow the fluid to exit the measurement chamber after having interacted with the plurality of analyte sensors; the measurement chamber defining a sample volume for accommodating the fluid to be analyzed, the sample volume extending at least between the inlet and the outlet; and heating element configured to heat the fluid accommodated within the measurement chamber;

wherein the heating element is disposed only at the first wall.

Disposing the heating element only at the first wall, in particular only on a single side of the measurement chamber, has been found to provide a sufficiently uniform heat distribution while maintaining low manufacturing costs and short measurement cycle times.

Embodiments and combinations thereof disclosed with reference to the first aspect of the invention may equally apply to the second aspect of the invention and vice versa.

In some embodiments the first wall has a first surface facing the second wall, and a second surface, opposite the first surface and facing away from the second wall; wherein the heating element is disposed at the second surface of the first wall, e.g. disposed on or integrated into the first wall. Accordingly, a particularly efficient heating of the contents of the measurement chamber is achieved.

Generally, the heating element may be any suitable element configured to dissipate heat towards the sample fluid in the measurement chamber.

The heating element may be a part of a heating system. The heating system may include the heating element and further components, such as a temperature control circuit and/or a temperature sensor and/or additional electrical circuitry. For example, the additional electrical circuitry may include electrical contact points and connecting wires for electrically connecting the heating element with the temperature control circuit. The temperature control circuit may comprise circuitry or devices for controlling the heating effect of the heating element, e.g. based on temperature measurements by a temperature sensor. The temperature control circuit may include one or more of the following components: an A/D converter, a duty cycle regulation circuit, a suitably programmed processing unit.

The heating element may be an electric heating element, such as a resistive heating element. In some embodiments, the heating element comprises a heating trace made from an electrically conductive material disposed at a surface of the first wall and extending between a first end point and a second end point. The heating trace may be deposited on the surface of the first wall or integrated into the first wall. In some embodiments, the measurement chamber only has a single heating trace. Accordingly, when a voltage is applied between the first and second end points, an electrical current flows through the heating trace. The resistivity of the heating trace causes heat to be dissipated by the heating trace. The current-induced heat dissipated by the heating trace thus heats the first wall and the contents of the measurement chamber. By controlling the applied voltage, the amount of heating may be controlled. Other examples of a heating element include semiconductor heating elements. For example, semiconductors may be positioned with variable distance between each other. Yet further examples of heating elements may utilize heating by means of microwaves, infrared radiation and/or air systems.

In some embodiments, the sensor device or an analyzer apparatus into which the sensor device is inserted, may comprise a temperature control circuit configured to control the applied voltage. It will be appreciated that the voltage may be controlled in a number of ways, e.g. by increasing/decreasing the voltage or by applying the voltage in pulses and by varying the pulse width and/or the pulse density. Various embodiments of the sensor device described herein provide a highly responsive device allowing for an immediate and direct temperature control of the fluid in the sample volume. Power may be supplied to the heating element by any suitable means, such as by supplying DC or AC current to the heating element through electrically conducting leads or other forms of terminals, such as via an inductive coupling.

The heating trace may be arranged in a heating trace layout across an entire face of the first wall or only across a portion of a face of the first wall. In some embodiments, the heating trace may extend across at least a part of one or more further walls of the measurement chamber. In some embodiments, the heating trace is disposed in a layout having portions of alternate directions, such as a meandering layout, a zigzag layout, a serpentine layout or the like. Other examples of layouts include a helical layout.

In some embodiments, the heating trace layout defines a trace density as a length of heating trace per unit surface area. In some embodiments, the trace density is higher in a proximity of the inlet than in a proximity of the outlet, thereby causing a higher heating power in a proximity of the inlet than in a proximity of the outlet. In particular, in some embodiments, the trace density is higher along a first portion of the measurement chamber between the inlet and a reference position along the flow path than along a second portion of the measurement chamber extending between the reference position and the outlet. Preferably, the reference position may be defined as the position of a temperature sensor. Alternatively, the reference position may be defined as a point halfway between the inlet and the outlet, or in another suitable manner. More particularly, in some embodiments, the first wall has an inlet wall portion extending from the inlet to the reference position along the flow path, and an outlet wall portion extending from the reference position to the outlet, and the trace density calculated for the entire inlet wall portion is higher than the trace density calculated for the entire outlet wall portion, such as at least more than a factor 1.0, such as at least a factor 1.1; 1.5; 2.0; 2.5; 3.0; 3.5; 4.0; 4.5; or 5.0 higher.

Alternatively or additionally, in some embodiments, the heating trace has an electric resistivity that varies along the heating trace. For example, the resistivity of the heating trace may be varied by varying a cross-sectional area of the heating trace along the length of the heating trace. The cross-sectional area may be varied by varying the height/thickness of the heating trace and/or by varying the width of the heating trace along the length of the heating trace. Yet alternatively or additionally, the resistivity of the heating trace may be varied by varying the heating trace material along the length of the heating trace, in particular by selecting heating trace materials of different specific resistivity.

In some embodiments the sensor device comprises a first substrate layer, in particular a first planar substrate layer, defining the first wall of the measurement chamber. Additionally, the sensor device may comprise a second substrate layer, in particular a second planar substrate layer, defining the second wall of the measurement chamber. The first and second substrate layers may be parallel to each other and the measurement chamber may be disposed between the first and second substrate layers. In particular, in some embodiments, the sensor device comprises an intermediate layer disposed between the first and second substrate layers, the intermediate layer accommodating the measurement chamber. For example, the intermediate layer may define a circumferential wall and the first and second substrate layers may define a top and a bottom wall, respectively. The intermediate layer may be made from a gasket material defining an aperture and opposite ends of the aperture may be covered by the first and second substrate layer, respectively.

In particular, in some embodiments, each of the inlet and outlet are formed as a respective orifice extending through the first substrate layer or the second substrate layer. For example, the measurement chamber may be made in a planar sandwich construction of two counter-stacked substrates/plates separated by a spacer with a recess defining a sample volume. The substrate may be made from ceramics or other suitable substrate material. The substrate may be flexible or rigid and may be constructed using, for example, standard PCB, flex PCB, PET, PI, ceramic, glass, etc. For example, the substrate may be made from an inert material such as a dielectric, pressure sensitive adhesive, laminate, etc. The spacer may be made from a polymer material or from another suitable material. The heating element, such as a heating trace, may be printed or otherwise deposited on a surface of the first and, optionally, the second substrate. When the inlet and the outlet are formed in one or both of the substrate layers, the spacer may form a closed circumferential wall of the measurement chamber. In alternative embodiments the inlet and/or the outlet may be formed in the spacer.

In some embodiments, the first substrate layer may have a width, measured in a direction across the length of the flow path between the inlet and the outlet of the measurement chamber, larger than a width of the measurement chamber. In particular, the first substrate layer may comprise a central layer portion and a peripheral layer portion, the central layer portion defining the first wall of the measurement chamber and the peripheral layer portion being laterally displaced from the measurement chamber, i.e. the surface of the peripheral layer portion does not delimit the measurement chamber. According to these embodiments, the measurement chamber defines a flow path that has a length defined between the inlet and the outlet of the measurement chamber and the heating trace comprises a peripheral trace portion and a central trace portion, the peripheral trace portion being disposed on a surface of the peripheral layer portion and the central trace portion being disposed on the central layer portion. In some embodiments, the peripheral trace portion is substantially uniformly distributed along the length of the flow path between the inlet end and the outlet end. Accordingly, the peripheral trace portion may provide a substantially uniform base heating effect along the length of the flow path. The central trace portion may be non-uniformly distributed along the length of the flow path, e.g. such that the trace density of the central trace portion is higher in a proximity of the inlet than in a proximity if the outlet. Accordingly, the central trace portion provides an additional heating effect that is higher in a proximity of the inlet than in a proximity of the outlet. In particular, in some embodiments, the central trace portion is only disposed in a portion of the measurement chamber proximal to the inlet, such as only between an inlet end of the chamber where the inlet is located and a reference position along the flow path, e.g. defined as the position of a temperature sensor or as a center of the measurement chamber.

In some embodiments, the sensor device comprises a temperature sensor, e.g. a thermistor element, which may be arranged in thermal contact with the sample in the measurement chamber. Alternatively, other types of temperature sensors may be used, e.g. a semiconductor temperature sensor or an infrared temperature sensor.

Accordingly, the sensor device, or an analyzer apparatus comprising the sensor device, may control the heating element responsive to the temperature of the measurement chamber as sensed by the temperature sensor. The control may e.g. be implemented by controlling the voltage applied to the heating element responsive to a signal from the temperature sensor. Alternatively, a thermistor integrated into the heating element may be used to provide a self-regulating heating element. In some embodiments, the temperature sensor is disposed at the first wall, e.g. at a surface of the first wall, such as the surface facing the sample volume. The temperature sensor may be attached to the surface or embedded into the wall. In some embodiments, the temperature sensor is disposed at a central portion of the measurement chamber, e.g. such that the distance between the temperature sensor and the inlet is substantially equal to the distance between the temperature sensor and the outlet, e.g. such that the difference between these distances is no more than 50% of the largest of the two distances, e.g. no more than 5%, 10%, 15%, 20%, 25%, 30%, 35%, 40%, or 45% of the largest of the two distances. Thereby a reliable temperature reading representative of the temperature of the fluid sample is achieved. In alternative embodiments, the temperature sensor is positioned proximal to the outlet or proximal to the inlet. In some embodiments, the temperature sensor is positioned at a portion of the first wall not covered by the heating element, e.g. more than 0.5 mm displaced from the closest part of the heating element, such as more than 1.0 mm, 1.5 mm, 2.0 mm; 2.5 mm, 3.0 mm, 3.5 mm, 4.0 mm, 4.5 mm, or 5.0 mm displaced from the closest part of the heating element.

The inventors have realized that such positions allow for a control of the heating element such that a particularly uniform temperature distribution is achieved.

In some embodiments, the sensor device comprises only a single heating element, e.g. a single heating trace, and/or only a single temperature sensor. It has turned out, that a single heating element and/or only a single temperature sensor may be sufficient for achieving a uniform temperature distribution while maintaining a low cost sensor device. In alternative embodiments, the sensor device comprises more than one heating element and/or more than one temperature sensor. For example, an even closer temperature regulation may be achieved by providing two or more zones within the measurement chamber, each zone having its own heating element and temperature sensor.

In some embodiments, the fluid accommodated in the measurement chamber may be held stationary inside the measurement while the fluid interacts with the analyte sensors, e.g. by closing the inlet and/or outlet of the sensor device. In other embodiments, the fluid may interact with the analyte sensors while the fluid flows along the measurement chamber from the inlet to the outlet, thus not requiring the fluid to be held stationary. According to some embodiments, measurement may be initiated after filling the measurement chamber has been completed, optionally after a further delay time.

In some embodiments, during operation of the sensor device, the measurement chamber may be filled with the sample fluid so as to allow the fluid to contact or otherwise interact with the analyte sensors and with the purpose of performing a measurement on the fluid sample. In some embodiments, some or all of the analyte sensors are non-contact analyte sensors that do not require physical contact between the analyte sensor and the sample fluid.

According to some embodiments, the sensor device is adapted to measure one or more analytes in a fluid sample so as to determine a corresponding parameter of the analyte, such as pH, concentrations of electrolytes, concentrations of metabolic factors or concentrations of enzymes. The fluid sample may be a biological sample, such as a body fluid, i.e. a physiological fluid.

Examples of biological samples may include liquid samples and/or gas samples. Liquid samples may include a body liquid. Liquid samples may be selected from the group of blood, diluted or undiluted whole blood, serum, plasma, saliva, urine, cerebrospinal liquid, pleura, synovial liquid, ascites liquid, peritoneal liquid, amniotic liquid, milk, dialysis liquid samples, or the like, as well as any quality control materials and calibration solutions used in analyzer equipment for measuring any of these fluids. Gaseous samples may include respiratory gas, expiratory air, or the like, as well as any quality control and calibration materials used in analyzer equipment for measuring any of these fluids. Accordingly, in some embodiments, the sensor device is configured for analyzing parameters of liquid samples, such as body liquids. The sample may be treated prior to testing in order to make it more amenable to being tested. Pretreatment methods may include one or more of the following: mixing, dilution, filtration, concentration, extraction, removal or inactivation of components which might interfere with the results, and/or addition of reagents. Examples of other biological samples include fermentation broths or microbial cultures, waste water, food products, and the like.

Examples of parameters in respect of analytes which may be determined by means of at least some embodiments of the sensor device disclosed herein include: $pO_2$, $pCO_2$, pH; concentrations of electrolytes such as $Li^+$, $Na^+$, $K^+$, $Ca^{2+}$, $Mg^{2+}$, $Cl^-$, $HCO^{3-}$ or $NH_3$ ($NH_4^+$); concentrations of metabolic factors, such as glucose, creatinine, urea (BUN), uric acid, lactic acid, pyruvic acid, ascorbic acid, phosphate or protein; concentrations of enzymes such as lactic acid dehydrogenase, lipase, amylase, choline, esterase, alkaline phosphatase, acid phosphatase, alanine amino transferase, aspartate, amino transferase, or creatinine kinase.

Further according to some embodiments, the sensor device is adapted for measuring a partial pressure of a gas in the fluid sample, such as $pO_2$, or $pCO_2$.

The sensor device, and/or an analyzer comprising the sensor device, may comprise a measurement system, e.g. comprising electrical circuits, one or more detectors, sensor readout instrumentation, signal processing circuitry, and/or the like. During operation, the measurement system may be configured to read out signals from the analyte sensors, process the signals and determine a measurement result. It will be appreciated that some or all of the analyte sensors may share at least some components of the measurement system while other components of the measurement system may be specific to individual analyte sensors. In this description, the term analyte sensor denotes any sensor capable of measuring a physical parameter of the sample fluid, such as the presence and/or concentration of a chemical substance present in the sample fluid. It will be appreciated that a sensor device and/or analyzer may comprise one or more different types of analyte sensors, such as optical sensors, electrochemical sensors, and/or sensors utilizing other sensing technologies. It will be appreciated that, in some embodiments, the components of the measurement system may be distributed between the sensor device and the analyzer into which the sensor device may be inserted. For example, some or all of the measurement circuits, excitation sources, detectors and/or the like may be arranged in the analyzer allowing for a relative simple sensor device.

Each analyte sensor may define a respective sensing area, e.g. at an inwardly facing surface of the measurement chamber. Each sensing area may be a portion of the inwardly facing surface. When the sample fluid interacts with the sensing area, the analyte sensor may be configured to detect a result of the interaction, e.g. as an optical or electrical signal. The sensing areas may be arranged at respective locations throughout the measurement chamber.

The present disclosure relates to different aspects including the sensor devices described above, corresponding apparatus, systems, methods, and/or products, each yielding one or more of the benefits and advantages described in connection with one or more of the other aspects, and each having one or more embodiments corresponding to the embodiments described in connection with one or more of the other aspects and/or disclosed in the appended claims.

According to one aspect, described herein are embodiments of an analyzer apparatus comprising a sensor device retaining mechanism, in particular a receptacle, configured to receive an embodiment of a sensor device as described above or in the following.

In some embodiments, the sensor device comprises a housing accommodating at least the measurement chamber, such as at least the first and second substrate layers; wherein the housing comprises an opening exposing a portion of a surface of one of the walls of the measurement chamber, in particular a wall other than the first wall, such as a portion of the second substrate layer, said exposed portion facing away from the sample volume. Accordingly, in some embodiments, the sensor device retaining mechanism comprises a heat reservoir element defining a heat exchange member configured to extend through the opening and be brought into heat exchange contact with the exposed portion of the wall, such as of the second substrate layer, when the sensor device is received by the sensor device retaining mechanism. Accordingly, a more uniform and accurate heating may be achieved.

In some embodiments, the sensor device retaining mechanism comprises:

a conduit configured to be brought into fluid communication with the inlet of the sensor device when the sensor device is received by the sensor device retaining mechanism; and a heating element configured to pre-heat fluid flowing through said conduit towards the inlet of the sensor device.

Some embodiments of an analyzer apparatus may be configured to analyze liquid samples. To this end, some embodiments of an analyzer apparatus include a liquid handling system which may include one or more valves, conduits, and/or pumping/transfer means, for controlling liquid flow, such as for filling and emptying of the measurement chamber with the liquid sample—preferably in an automated or semiautomated manner.

Further, according to some embodiments, the fluid sample is a gas, e.g. a medical gas, such as a physiological gas. Some embodiments of the analyzer apparatus may thus be adapted to analyzing parameters of medical gas samples. Examples of particularly useful medical gas samples are selected from the group of respiratory gas, expiratory air, or the like, as well as any quality control and calibration materials used in analyzer equipment for measuring any of these fluids. Some embodiments of the analyzer apparatus may thus include a gas handling system comprising one or more valves, conduits, and/or pumping/transfer means, for controlling gas flow, such as for filling and emptying of the measurement chamber with the gas sample—preferably in an automated manner. In some embodiments, the analyzer apparatus comprises fluid handling means suited for both liquid and gas.

The analyzer apparatus and/or the sensor device may comprise a temperature control circuit configured to receive a signal from the temperature sensor of the sensor device and to control the heating element responsive to the received signal from the temperature sensor, e.g. so as to minimize a difference between the received signal from the temperature sensor and a target value. The temperature control circuit may be embodied by a control unit configured to control operation of the analyzer such as operation of the analyte sensors and/or sample handling system, etc.

In some embodiments, the sensor device may be a disposable and/or single-use device which may be for use as a stand-alone device or in combination with an analyzer apparatus.

BRIEF DESCRIPTION OF THE DRAWINGS

Preferred embodiments of the invention will be described in more detail in connection with the appended drawings, where:

FIG. 2 schematically shows an example of a sensor device.

FIG. 3 schematically shows a top view of an example of a second substrate layer.

FIG. 4 schematically shows a top view of an example of an intermediate layer.

DETAILED DESCRIPTION

Figure 1:
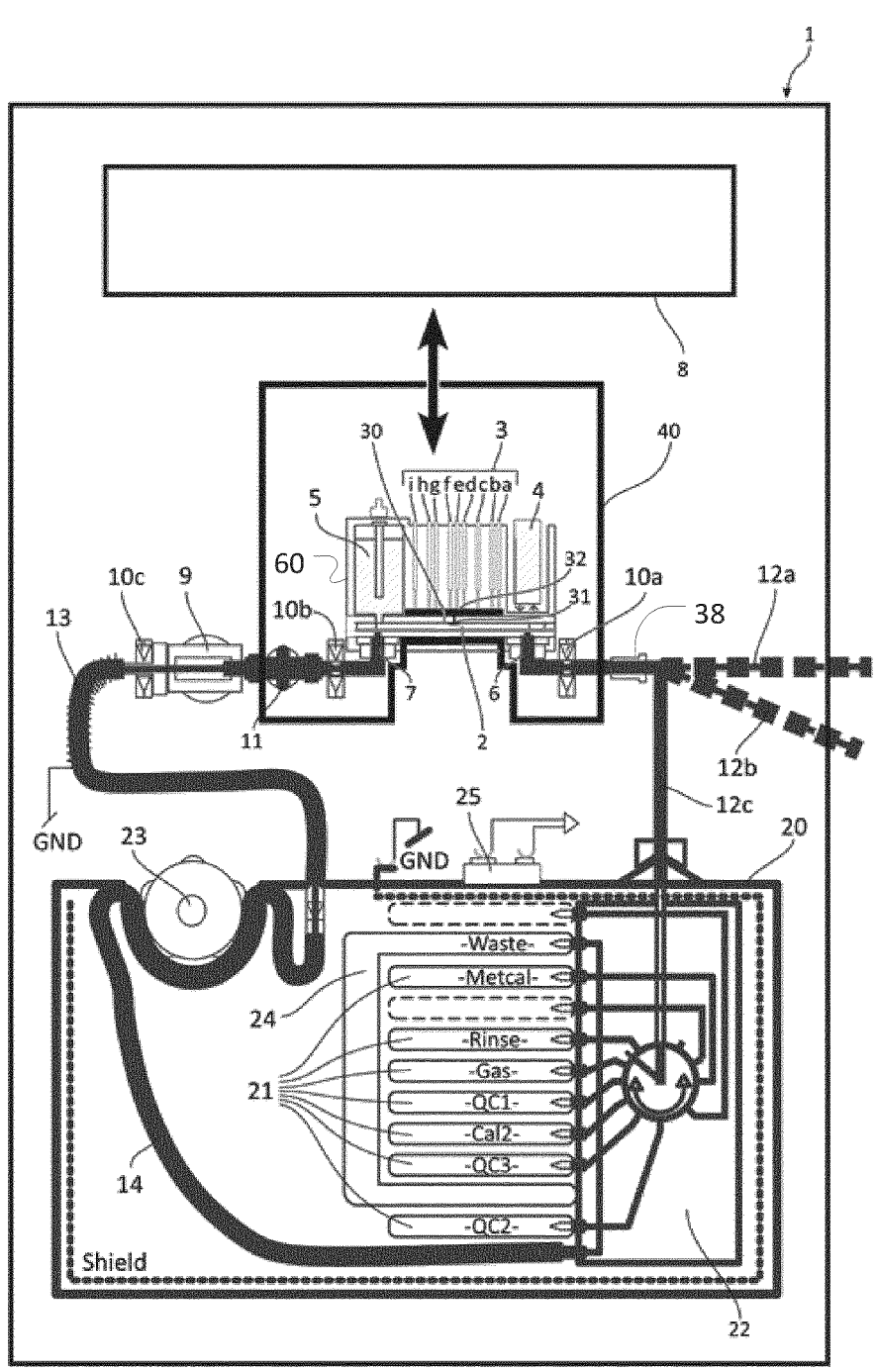
FIG. 1 shows a schematic diagram of a blood analyzer including a sensor device.

FIG. 1 schematically shows an example of an apparatus 1 for the analysis of biological liquid samples, such as body liquids. The apparatus 1 is in some embodiments configured for the analysis of biological fluid samples, such as medical gas samples and/or body fluids. The apparatus 1 has a sensor device 60, a liquid handling system 20 and a processing unit 8.

The sensor device 60 has a measurement chamber 2, which is equipped with one or more analyte sensors that can be read out via contact pins. To this end, the sensor device comprises contact pins 3(a-i) for establishing electrical contact with sensor electrodes, and a reference electrode 5. In the example of FIG. 1, the sensor device 60 is a replaceable sensor cassette that can be inserted into an enclosure 40 of the analyzer and that can be removed again from the analyzer at the end of its operational life. In the example of FIG. 1, the sensor device comprises a $pO_2$ measuring system 4.

The liquid handling system 20 is adapted for feeding a liquid sample to the sample volume of the measurement chamber 2 through an inlet 6 of the measurement chamber and for removing the liquid sample through an outlet 7 of the measurement chamber 2.

The sensor device 60 has a heating element 32 arranged in good thermal contact with the measurement chamber. In particular, the heating element is arranged on a surface of a substrate 30 that forms a top wall of the measurement chamber 2. An example of a measurement chamber will be described in more detail with reference to FIG. 2 below. The sensor device 60 further has a temperature sensor 31, here a thermistor, which is arranged on an inside surface of the measurement chamber 2 approximately half way between the inlet 6 and the outlet 7. The temperature sensor 31 is for measuring the temperature of a liquid sample inside the measurement chamber, and for providing the measurement result to the processing unit 8.

The processing unit 8 is configured to control operation of the sensor device 60 and the liquid handling system. In particular, the processing unit 8 controls operation of the heating element 32 in response to the temperature reading from the temperature sensor 31 so as to bring the sample temperature in agreement with a target temperature at which measurements are to be performed. It will be appreciated that in alternative embodiments, temperature control may be performed by a separate temperature controller which may be separate from the processing unit 8.

The processing unit 8 is further adapted to receive flow data from the liquid handling system 20 and/or measurement data from the analyte sensors of the sensor device 60. The processor unit 8 comprises programmed instructions for performing suitable signal and data processing tasks including data acquisition, process control and/or the like.

For example, the processing unit may be configured to determine an initial temperature of the liquid sample entering the measurement chamber 2, e.g. based on flow data from the liquid handling system 20 and/or from sample heating data based on signals from temperature sensor 31.

For performing measurements, a user may provide a liquid sample at an input port of the apparatus 1, which, in the example of FIG. 1, can be brought into two positions 12a/b. However, other embodiments may have different types of input ports. The liquid sample is transferred through the inlet 6 to the measurement chamber 2. Optional preheating of the blood sample is ensured by an optional preheater 38. The preheater may be a tube placed upstream from the sensor device. The preheater may be heated electrically or by heat transferred from a heat reservoir, e.g. a sensor device retainer, to the preheater via direct contact. When the sample has entered the measurement chamber, the sample is heated to a desired target temperature by means of heating element 32. The liquid sample contacts or otherwise interacts with respective analyte sensors. The analyte sensors are in one embodiment arranged to provide essentially simultaneous measurements on analyte parameters in the liquid sample, e.g. a whole blood sample. Preferably, the required sample amount for obtaining precise and reliable analysis data is as small as possible. A detailed example of a sensor assembly design that is particularly suitable for simultaneously measuring a plurality of different parameters in bodily fluids, particularly in whole blood, and its use in a blood analyzer is e.g. found in EP 2 147 307 B1 or in U.S. Pat. No. 8,728,288 B2.

For example, one type of analyte sensor comprises an electrochemical sensor. An electrochemical sensor may comprise one or more analyte electrodes and a reference electrode. An electrochemical sensor may comprise one or more membranes. An electrochemical sensor may comprise one or more electrically responsive components configured to provide an electrical response when brought into contact with a fluid in the measurement chamber that includes an analyte to which the electrically responsive component is responsive.

Other examples of an analyte sensor comprise an optical sensor 4 with a sensor layer which may interact with the sample fluid accommodated in the measurement chamber. The sensor layer is sensitive to an amount of an analyte present in the fluid sample that is provided in the measurement chamber. The optical sensor further comprises instrumentation for the optical readout of the sensor layers' response to the presence of the analyte. The readout instrumentation typically comprises a device for providing a stimulus to the sensor layer. The readout instrumentation may further comprise a detector and/or optical elements, such as lenses and/or optical wave guiding components for collecting radiation emitted from the sensor layer in response to the stimulus, and further for transferring the collected luminescence radiation to a detector of the optical sensor. The stimulus is typically a radiation source, such as a laser or light emitting diode (LED), arranged and configured to provide optical probing radiation to the sensor layer.

The optical sensor may further comprise optional components for optically selecting and/or analyzing the radiation collected from the sensor layer, such as optical filters and/or optical amplifiers, before the light is received by the detector. The detector converts the detected luminescence radiation to a corresponding signal. The optical sensor is thus configured to provide a signal representative of the amount of the analyte for which it is sensitized.

The signal from the optical sensor and/or electrochemical sensor and/or from other analyte sensors of the analyzer are provided to the processing unit 8 of the sample analyzer for analog and/or digital signal processing. The processing unit may store measurement data in a storage device of the analyzer, display the measurement data on a display of the analyzer and/or provide the measurement data at an output, e.g. a communications interface, of the analyzer.

It will be appreciated that multiple analyte sensors may share some or all of the readout instrumentation but comprise respective sensor layers that define respective sensing areas. It will further be appreciated that at least some of the components of the readout instrumentation may be disposed in the analyzer. To this end, the sensor device may comprise suitable interfaces, such as electrical and/or optical interfaces so as to allow the readout instrumentation of the analyzer to cooperate with the sensing layers of the sensor device.

In some embodiments, one or more sensing areas are provided by sensor layers of respective analyte sensors. Each sensor layer may define a sensor surface forming a front side interface towards the measurement chamber. During the measurement, the front side interface may be in contact with the fluid sample. Optical and/or other probing may be performed from the back side of the sensor layer, i.e. from the side facing away from the sample fluid. To this end, the sensor layer may be transparent or translucent. A stimulus may be given, typically in the form of excitation light that is directed to the sensor layer from the backside, so as to produce an excited fraction of the luminophor in the sensor layer. The excited luminophor molecules relax back to a ground state under the emission of luminescence light, which may also be observed from the back side. The optical sensor therefore further comprises instrumentation for detecting and registering luminescence emitted from the luminophor, and thus to observe the sensor layer response to the applied stimulus.

Following pre-programmed instructions loaded in the processing unit 8 and/or based on user input, measurements are performed using the analyte sensors. The analyte sensors generate quantitative signals that are representative of a physical parameter for the respective analyte and provide the signals to the processing unit 8. The processing unit 8 is adapted to receive and process signals from the analyte sensors and present the processed signals as output to a user and/or to a subsequent/further data analysis. After measurement, the liquid sample is discharged, and the measurement chamber 2 is prepared for the next measurement.

The embodiment of the apparatus 1 shown in FIG. 1 is particularly adapted for the measurement of blood parameters, and further comprises an optional oximetry measurement device 9 downstream of the measurement chamber 2. Performing the measurements, calibration tasks, and quality control procedures thus typically involves the loading, unloading, rinsing, cleaning and re-loading of different liquids, which may be done using the infrastructure of the liquid handling system 20. The liquid handling may be controlled in an automated way by the processing unit 8 according to pre-programmed instructions and/or user input. The liquid handling system 20 includes a number of reservoirs 21 pre-filled with process liquids (here denoted RINSE/CAL1, CAL2, QC1, QC2, QC3, METCAL, GAS) for rinsing/wash-out, calibration and quality control tasks. The process liquids (RINSE/CAL1, CAL2, QC1, QC2, QC3, METCAL, GAS) have a known composition. The exact composition of a given batch may be stored in a chip 25 that may be attached to a cassette comprising the reservoirs 21, wherein the chip 25 may be read by the processing unit 8. The process liquid (RINSE/CAL1, CAL2, QC1, QC2, QC3, METCAL, GAS) for a given process step may be selected by a fluid selector valve 22, and via feed line 12c transferred through the inlet 6 to the measurement chamber 2. Correct filling of the measurement chamber 2 may be monitored and verified by visual inspection or according to known procedures by observing the propagation of a liquid interface through the system by means of liquid sensors 10a, 10b, 10c located upstream and downstream of the measurement chamber, such as at the inlet 6 (liquid sensor 10a), at the outlet 7 (liquid sensor 10b), and just after the oximetry measurement device 9 (liquid sensor 10c), respectively. The fluid flow through the apparatus 1 is driven by a pump 23, here a peristaltic hosepump arranged downstream of the measurement chamber 2 and the oxygenation measurement device 9 and connected thereto via fluid line 13. The discharged fluids are finally transported through fluid line 14 to the waste reservoir 24.

The analyser apparatus 1 comprises an enclosure 40 for accommodating the sensor device 60. The walls of the enclosure 40 form a housing with walls and a retaining mechanism for retaining the sensor device and for providing suitable interfaces for fluid transfer to and from the sensor device and for communicating sensor signals and/or data from the sensor device and for providing operating power to the heating element. The walls of the enclosure may be held at a fixed temperature so as to provide a thermal shield and for maintaining the immediate environment of the sensor device at a constant temperature.

FIG. 2 schematically shows a more detailed view of an example of a sensor device, e.g. for use in the analyzer of FIG. 1.

The sensor device, generally designated 60, comprises a housing 61 which accommodates the various components of the sensor device. The housing may be made from plastic or from another suitable material.

The sensor device has a measurement chamber 2 that defines a sample volume 21. In this example, the measurement chamber is formed as a sandwiched construction comprising substrate layers 30 and 33 and gasket layer 34. However, it will be appreciated that other designs of measurement chambers are possible as well.

The measurement chamber comprises a first substrate 30 and a second substrate 33 defining top and bottom walls of the measurement chamber 2. The measurement chamber further comprises an intermediate layer 34 made from a gasket material, e.g. a polymeric material. The intermediate layer may also be referred to as a spacer. The intermediate layer is disposed sandwiched between the first and second substrate layers. The intermediate layer defines side walls of the measurement chamber 2. The intermediate layer may define a recess, through-hole or similar void. It will be appreciated that the terms top wall, bottom wall and side wall as used herein are merely intended to allow easy distinction of the various walls of the measurement chamber; the skilled person will understand that, depending on the physical orientation of the measurement chamber in a sensor device, the walls may be oriented in different directions in space, i.e. the top wall does not need to be above the bottom wall etc. The first and second substrates may be ceramic substrates or they may be made from another suitable material.

The measurement chamber has an inlet 6 at an inlet end 216 of the sample volume and an outlet 7 at an outlet end 217 of the measurement chamber, opposite the inlet end. The inlet and the outlet may be positioned all the way at respective ends of the measurement chamber, as illustrated in FIG. 2. Alternatively, the measurement chamber may extend further than only between the inlet and the outlet, i.e. the inlet and/or the outlet may be positioned displaced from the end walls. In the example of FIG. 2, the inlet 6 and outlet 7 are formed as through holes in the second substrate 33. However, alternative arrangements of the inlet and/or outlet are possible. For example, one or both of the inlet and outlet may be formed as through holes through the first substrate layer or even through a side wall of the intermediate layer. The inlet 6 is in fluid communication with an inlet port 611 of the housing 61. The inlet port allows the sensor device to be coupled to a corresponding feed port 56 of the liquid handling system 20 of an analyzer. Similarly, the outlet 7 is in fluid communication with an outlet port 71 of the housing 61. The outlet port allows the sensor device to be coupled to a corresponding return port 57 of the liquid handling system 20 of an analyzer.

The measurement chamber 2 has analyte sensors 39 for detecting respective analytes. In the example of FIG. 2, the analyte sensors are located at respective positions on the inner surface of the measurement chamber facing the sample volume 21. In particular, in the example of FIG. 2, some analyte sensors are positioned on the inner surface of the first substrate layer 30 and some analyte sensors are positioned on the inner surface of the second substrate layer 33. The analyte sensors 39 may be read out electrically, optically and/or in another suitable manner apparent to the skilled person when faced with present disclosure. It will be appreciated that the number and types of analyte sensors may vary. While the measurement chamber of FIG. 2 has analyte sensors on both substrate layers, the skilled person will appreciate that, in some embodiments, all analyte sensors may be arranged at the same substrate layer. Moreover, some or even all analyte sensors may be otherwise arranged at respective positions across the measurement chamber.

The measurement chamber comprises an electric heating element 32 disposed on the outer surface of the first substrate layer 30, i.e. facing away from the sample and the measurement chamber 21. In alternative embodiments, the measurement chamber may comprise one or more heating elements at alternative or additional locations, e.g. on the second substrate layer, on the inner surface of the first or second substrate layer, i.e. facing the sample and the measurement chamber 21, embedded within the first substrate layer, and/or the like. The electric heating element has the form of a resistive heating trace disposed on the surface of, or integrated into the first substrate in a suitable heating trace layout. Different examples of heating trace layouts will be described in connection with FIGS. 5A-D below. The heating element receives electrical power via end points 301 and an electrical interface 36. The measurement chamber of this example includes only a single heating trace, disposed only on the first substrate layer.

The measurement chamber further comprises a thermistor 31 or another suitable temperature sensor. In the example of FIG. 2, the thermistor is positioned at the inner surface of the first substrate layer 30, approximately halfway between the inlet 6 and the outlet 7. In other embodiments, a temperature sensor may be positioned at a different location, e.g. on the second substrate and/or displaced from the center.

The measurement chamber may optionally comprise further components, e.g. electrical circuitry 35 and/or components associated with the analyte sensors, which may be disposed on the outer surface of the first substrate and/or at different locations of the sensor device 60. The electrical circuitry 35 may provide electrical contact between the electrical interface 36 of the sensor device and the various electrical components, such as the analyte sensors and/or the thermistor 31. The electrical interface 36 provides electrical connection with the processing unit 8 via a corresponding interface 58. It will be appreciated that, in some embodiments, electrical power and/or signals may be communicated between the sensor device and other components of the analyzer in a contactless manner, e.g. inductively.

The sensor device 60 is a replaceable sensor device that can be inserted into an analyzer apparatus. To this end, as schematically illustrated in FIG. 2, the analyzer apparatus may comprise a sensor device retaining mechanism 45, e.g. in the form of a recess, adapter, receptacle and/or the like. The sensor device retaining mechanism 45 may be part of an enclosure as described in connection with FIG. 1. The sensor device retaining mechanism 45 provides a feed port 56 and a return port 57 for providing fluid connections with the inlet 6 and the outlet 7 of the measurement chamber via respective inlet and outlet ports 611 and 71 of the sensor device. The analyzer further provides an electric interface 58 for connecting the heating element 32 and the thermistor 31 with the processing unit 8 of the analyzer via a corresponding electric interface 36 of the sensor device. The interfaces 36 and 58 may also serve to communicate sensor signals from the analyte sensors of the sensor device in response to the liquid sample interacting with the analyte sensors 39 of the measurement chamber. The interface 58 may e.g. be located in the retaining mechanism or at a different suitable location, e.g. at a lid portion or other portion of an enclosure for accommodating the sensor device. When the electric interface is positioned on a side of the sensor device opposite the side where the inlet and outlet are positioned, the risk of a potential liquid spill affecting the electric interface is reduced.

The sensor device retaining mechanism 45 may further serve to maintain a constant temperature of the measurement chamber 2. To this end, the sensor device retaining mechanism comprises a heat transfer block 41 that is shaped and sized so as to extend through a corresponding opening in the housing of the sensor device such that the heat transfer block 41 is brought into direct contact with the second substrate layer 33 when the sensor device is inserted into or otherwise connected to the sensor device retaining mechanism 45. The sensor device retaining mechanism 45 thus conducts heat directly to the measurement chamber. As mentioned above the sensor device retaining mechanism may be part or an enclosure which may further comprise a thermal lid (not explicitly shown) such that the sensor device is accommodated inside an enclosure which may contribute to the thermal environment around the sensor device and prevent heat from being led away from the sensor device. The sensor device retaining mechanism 45 may further comprise a heater and, optionally, a temperature sensor such as a thermistor. The provision of a heat transfer block 41 in contact with the second substrate layer may be particularly useful in embodiments where the measurement chamber only comprises a heating element at the first substrate.

FIG. 3 schematically shows a top view of an example of a second substrate layer, e.g. of the measurement chamber of FIG. 2. The second substrate layer 33 comprises through holes defining an inlet 6 and an outlet 7, respectively.

FIG. 4 schematically shows a top view of an example of an intermediate layer, e.g. of the measurement chamber of FIG. 2. The intermediate layer 34 comprises a gasket material, e.g. a polymer material, defining side walls of a sample volume 21. The intermediate layer forms a spacer separating the first and second substrate layers.

FIGS. 5A-D schematically show top views of an outer surface of respective examples of a first substrate layer, e.g. of the measurement chamber of FIG. 2, seen from the side facing away from the measurement volume.

The first substrate layer 30 has a temperature sensor, e.g. a thermistor, disposed on its inner surface, located centrally with respect to the assembled measurement chamber. The position of the temperature sensor is indicated by a square 31 in FIGS. 5A-D. In particular, the temperature sensor is located such that its distance from the inlet end is approximately equal to its distance from the outlet end. The temperature sensor is also positioned such that it is substantially equally far from the lateral sides of the measurement chamber.

The first substrate layer 30 further comprises a single resistive heating element 32 formed as a heating trace extending between end points 301A and 301B. The heating trace extends in a meandering/serpentine trace layout across the outer surface of the first substrate layer. The heating traces may be disposed, e.g. printed, on top of the surface or be integrated into the substrate layer.

In FIGS. 5A-D, the extent of the sample volume as defined by the intermediate layer when the first substrate is assembled with the intermediate layer, is indicated by dashed line 21. The sample volume is an elongated volume extending between an inlet end, located proximate to the inlet of the measurement chamber when the first substrate layer is assembled with the other components to form the measurement chamber, and an outlet end, located proximate to the outlet of the assembled measurement chamber. The positions of the inlet and the outlet are indicated by circles 6 and 7, respectively, in FIGS. 5A-D.

The examples of FIGS. 5A-D have their heating traces arranged in different trace layouts. In all examples, the trace layout includes a peripheral portion 303 extending along the longitudinal sides of the measurement chamber 21 all the way between the inlet 6 and the outlet 7. The peripheral portions 303 of the trace layout are located outside the footprint of the measurement chamber, i.e. laterally displaced from the measurement chamber.

Figures 5A, 5B, 5C, 5D:
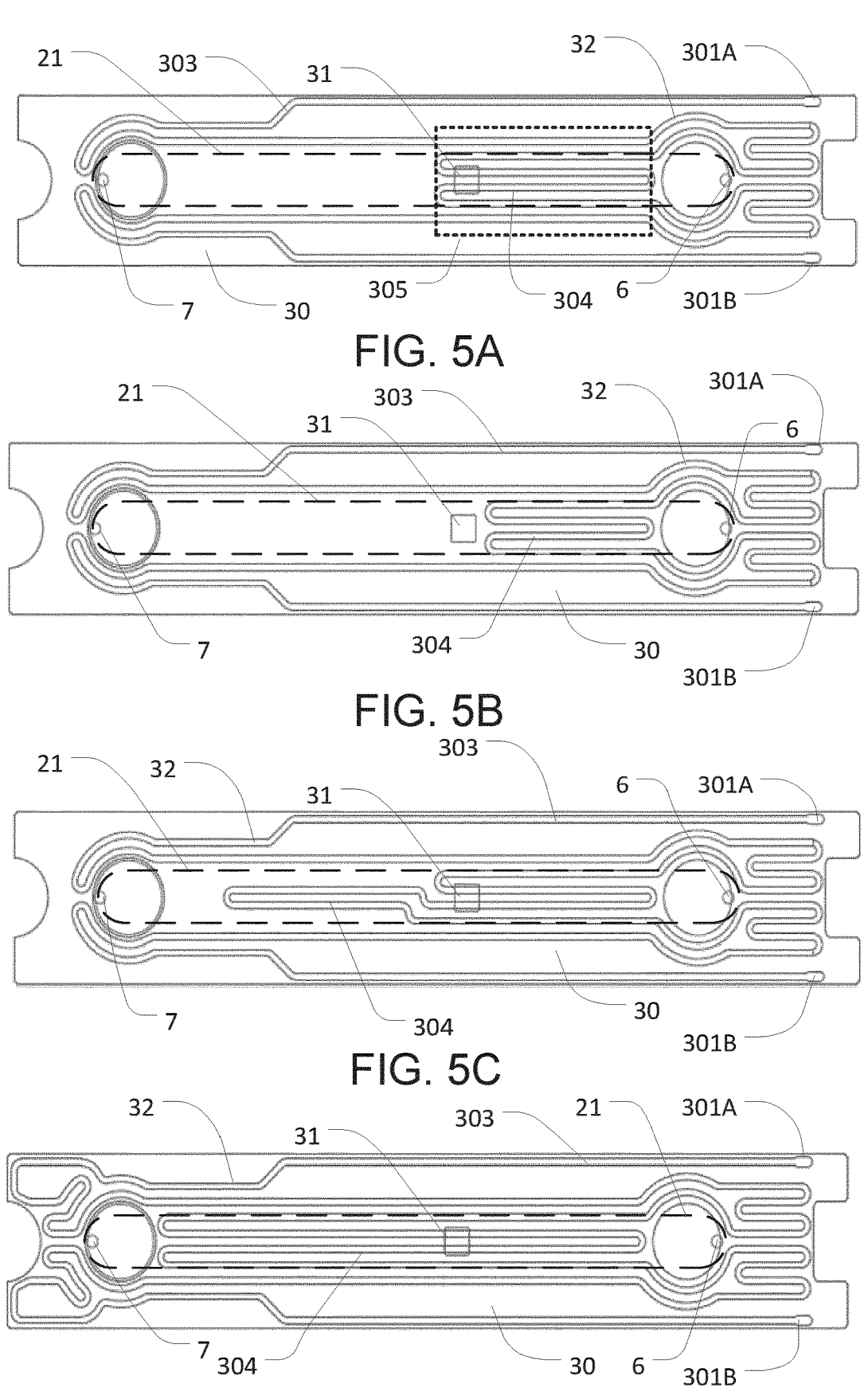
FIGS. 5A-D schematically show top views of an outer surface of respective examples of a first substrate layer.

The trace layout also includes a central portion 304 located inside the footprint of the measurement chamber 21. In the examples of FIGS. 5A-D, the central portion 304 of the trace layout extends to different degrees across the length of the measurement chamber and, in particular, along the flow path between the inlet 6 and the outlet 7:

In the example of FIG. 5A, the central portion of the trace layout only covers about half the length of the measurement chamber, in particular only the half proximate to the inlet 6, while the other half of the wall of the measurement chamber, proximate to the outlet 7, is free from any heating trace. In the example of FIG. 5A, the heating trace 32 extends beyond the position of the temperature sensor 31, i.e. the portion of the inner surface of the first substrate in the vicinity of the temperature sensor 31 is covered by heating trace. In some embodiments, the entire length of heating trace has a uniform resistivity per unit length, i.e. the heating effect per unit length of the heating trace is substantially uniform along the length of the heating trace, i.e. the heating effect of the heating element is higher in areas of the substrate layer with a high heating trace density (measured as length of heating trace per unit surface area) than in areas with low heating trace density. Accordingly, the heating element 32 of the substrate layer of FIG. 5A provides a higher heating effect at the half of the measurement chamber that is proximate to the inlet 6 and a lower heating effect at the half of the measurement chamber that is proximate to the outlet 7.

In an alternative embodiment, the resistivity per unit length of the heating trace may vary along its length. For example, the heating trace may be provided with a different resistivity per unit length within the area indicated by a dotted line 305, e.g. by altering the trace material and/or the cross-sectional area of the heating trace.

The trace layout shown in FIG. 5B is similar to the one of FIG. 5A, except that the central portion 304 of the trace layout covers less than half the length of the sample volume and, in particular, less than half the length of the flow path between the inlet and the outlet. In particular, the location of the temperature sensor 31 is not covered by heating trace.

In the trace layout shown in FIG. 5C, the central portion of the trace layout covers most of the length of the measurement chamber and, in particular, most of the length of the flow path between the inlet and the outlet. However, in the half of the footprint of the measurement chamber closest to the inlet 6 the trace density is higher than in the half closest to the outlet 7.

Hence, in all examples of FIGS. 5A-C, the laterally central portion of the trace layout has a higher trace density in the half of the footprint of the measurement chamber closest to the inlet 6 than in the half closest to the outlet 7.

FIG. 5D shows an example of the trace layout where the heating trace extends substantially uniformly across the entire length of the measurement chamber and, in particular, along the entire length of the flow path between the inlet 6 and the outlet 7. This example was used as a reference in the comparative tests described below.

Figure 6:
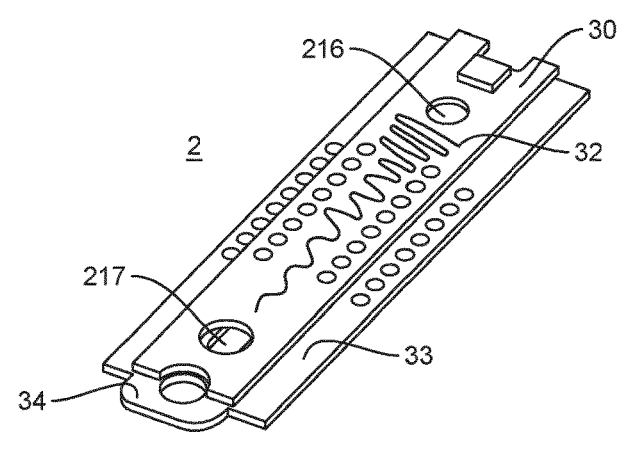
FIG. 6 schematically shows another example of a measurement chamber.

FIG. 6 schematically shows another example of a measurement chamber. The measurement chamber 2 of FIG. 6 is similar to the measurement chamber described in connection with FIG. 2 in that is formed as a layered structure comprising a first substrate layer 30, in intermediate layer 34 and a second substrate layer 33 all as described in connection with FIG. 2. The first substrate element 34 comprises a heating element 32 formed as a heating trace extending between the inlet end 216 and the outlet end 217 of the measurement chamber. The heating trace is arranged in a meandering/serpentine layout such that the trace density is higher in a proximity of the inlet end 216 than in a proximity of the outlet end 217.

Example

Sensor devices with measurement chambers having resistive heating elements with different heating trace layouts have been compared.

The sensor devices were of the type described in connection with FIGS. 2-5. Four different examples of measurement chambers were manufactured. The examples were identical except for the heating trace layout on the first substrate layer:

Example A had a first substrate layer as shown in FIG. 5A with a uniform resistivity of the heating trace.

Example B had a first substrate layer as shown in FIG. 5B with a uniform resistivity of the heating trace.

Example C had a first substrate layer as shown in FIG. 5C with a uniform resistivity of the heating trace.

Example D had a first substrate layer as shown in FIG. 5A but with a nonuniform resistivity of the heating trace. In particular, the cross-sectional area of the heating trace and, hence, its resistivity, within the area indicated by line 305 was different from the cross-sectional area of the remainder of the heating trace. Alternatively or additionally, the resistivity may be varied by providing different material compositions in different parts of the heating trace.

Moreover, a reference measurement chamber (current state) was manufactured which was identical with the examples A-D except that the first and the second substrate layers had a substantially uniformly distributed heating trace as shown in FIG. 5D for the first substrate.

All measurement chambers were provided with four identical analyte sensors for measuring potassium ("K-sensor"). The K-sensor has been chosen as it has a high temperature dependency. By disposing the same type of sensor on different positions across the measurement chamber, differences in the measurement results are indicative of temperature differences in the sample liquid across the measurement chamber. The measurements were performed using a reference liquid with a predetermined potassium concentration.

All tests were performed with an ABL-90 analyzer from Radiometer Medical ApS, Denmark. The analyzers were equipped with a special software version, which can read all analyte sensors as K-sensors.

The heater resistance was measured for all measurement chambers before being set in the analyzer. All K-sensors were calibrated so that their coefficient of temperature sensitivity were known.

Several scenarios were tested as described in Table 1 below.

The analyzers were placed in a standard test laboratory at room temperature (around 25° C.) or in a temperature controlled room (set at different temperatures, i.e. 15° C. or 32° C.).

The samples analyzed were all samples of a rinse solution and were placed in an iced water bath (for samples at 0° C.) or in the controlled temperature room.

Measurements were taken at a high frequency (aspirate as soon as ABL90 is ready—max. 2 min between each start—10 measurements in a row).

TABLE 1

Tested scenarios

| | | Laboratory temperature | | |
|---|---|---|---|---|
| | | 15° C. | 25° C. | 32° C. |
| Sample temp. | 0° C. | Frequent aspiration | Frequent aspiration | Frequent aspiration |
| | 15° C. | Frequent aspiration Long aspiration | | |
| | 25° C. | | Frequent aspiration | |
| | 32° C. | | | Frequent aspiration |

FIGS. 7-12 show the average of the measured temperatures by the K-sensors for each sensor position and each heating trace layout at different environmental conditions. In FIGS. 7-12, the sensor positions are labelled "K", "Na" "pH", and "Ca", respectively (reflecting the types of sensors normally disposed at the respective positions of the measurement chamber). The heating trace layouts are labelled "TEMP_A" (Example A), "TEMP_B" (Example B), "TEMP_C" (Example C), "TEMP_D" (Example D) and "TEMP_REF" (Reference), respectively.

TABLE 2

The measurement results for the respective figures

Figure 7:
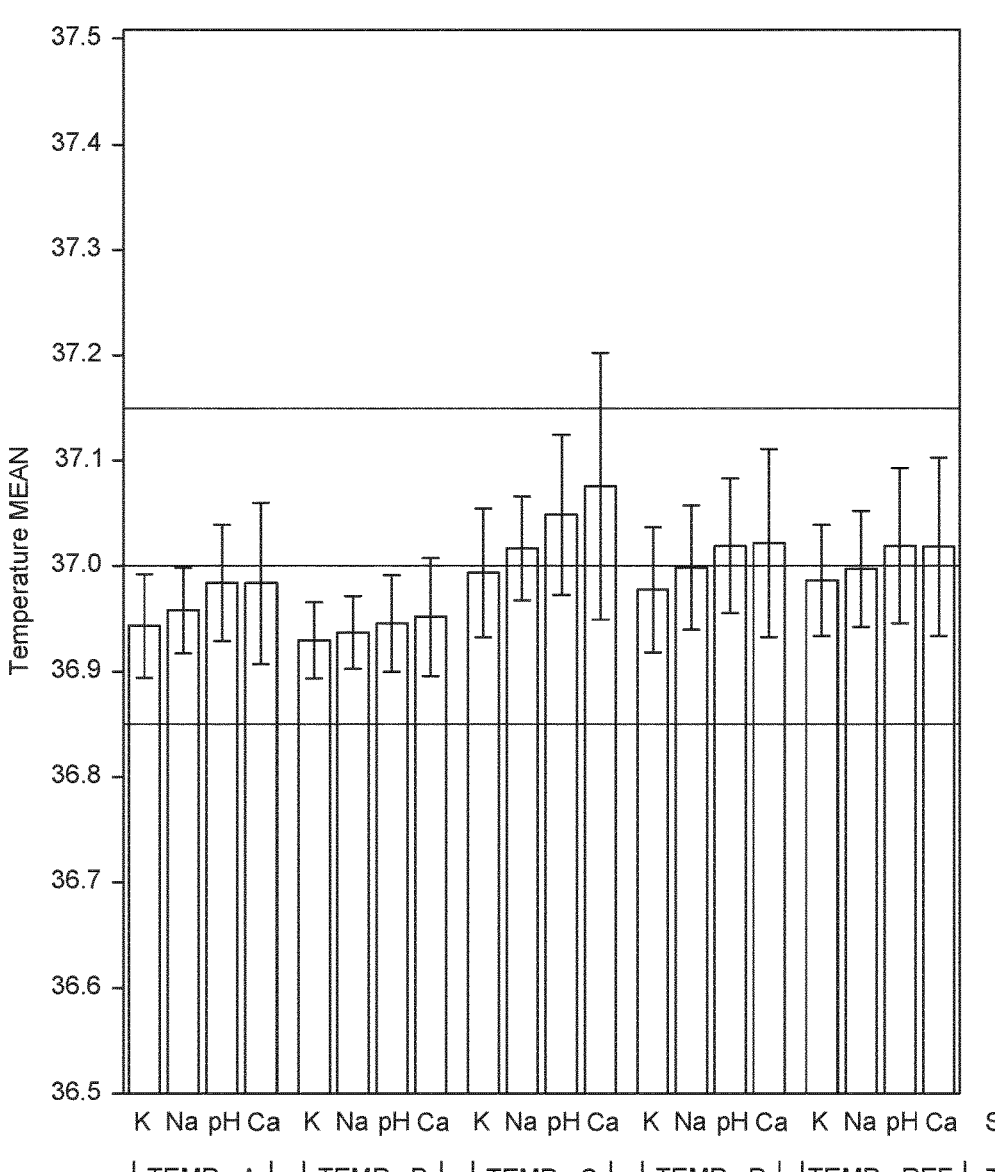
FIGS. 7-12 show results of comparative temperature measurements for different examples of measurement chambers having different heating element designs.
Figure 8:
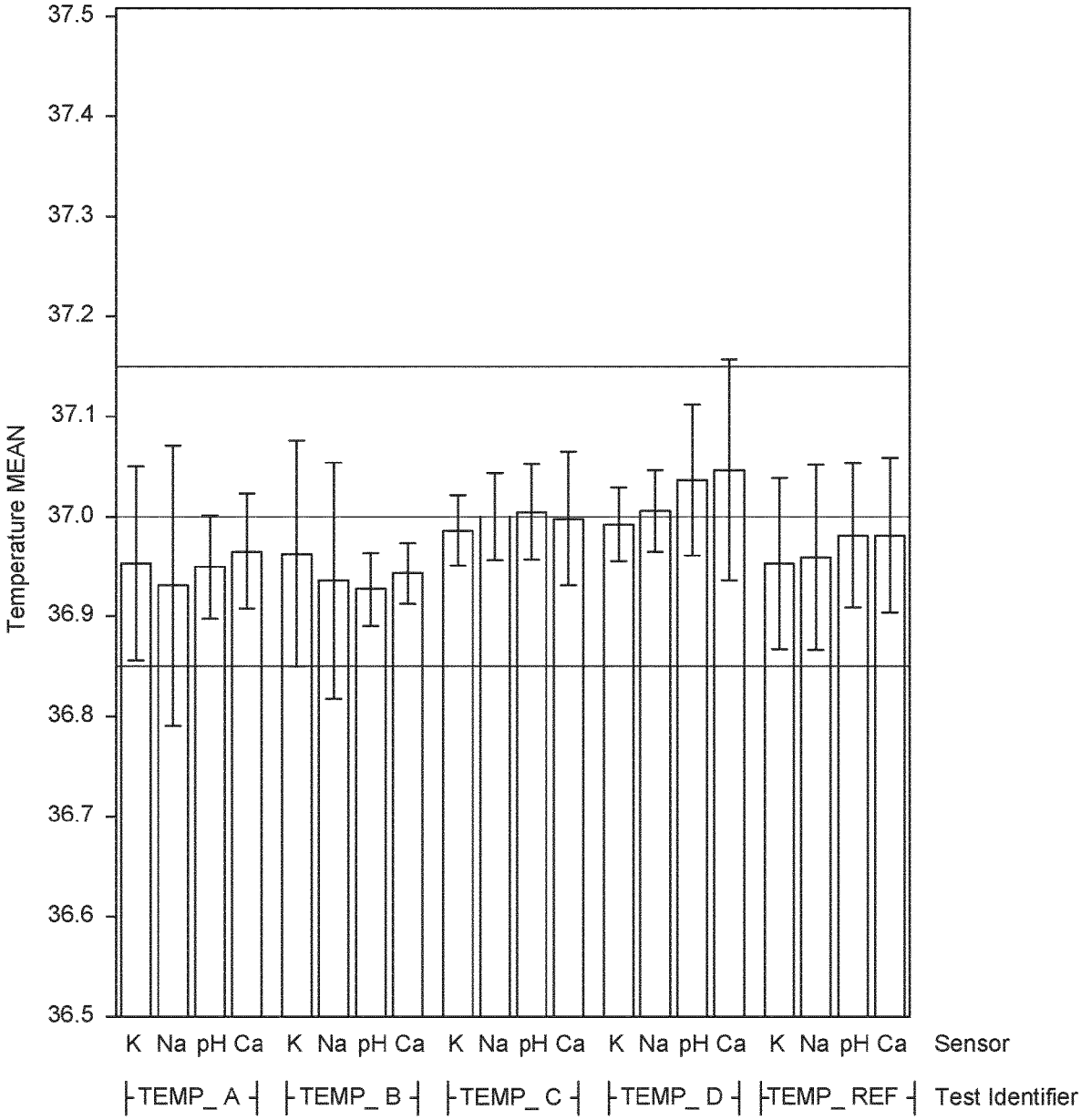
Figure 9:
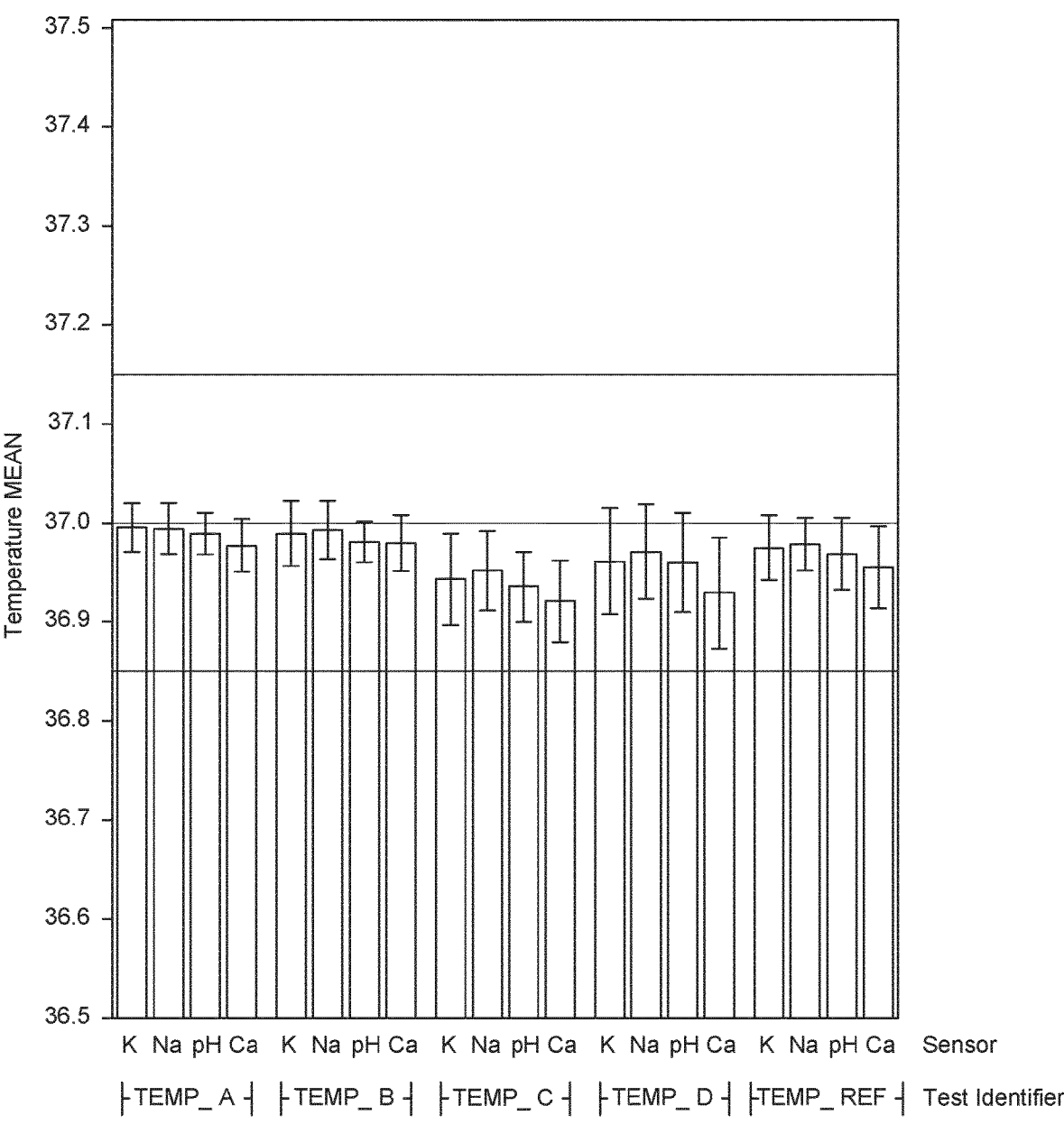
Figure 10:
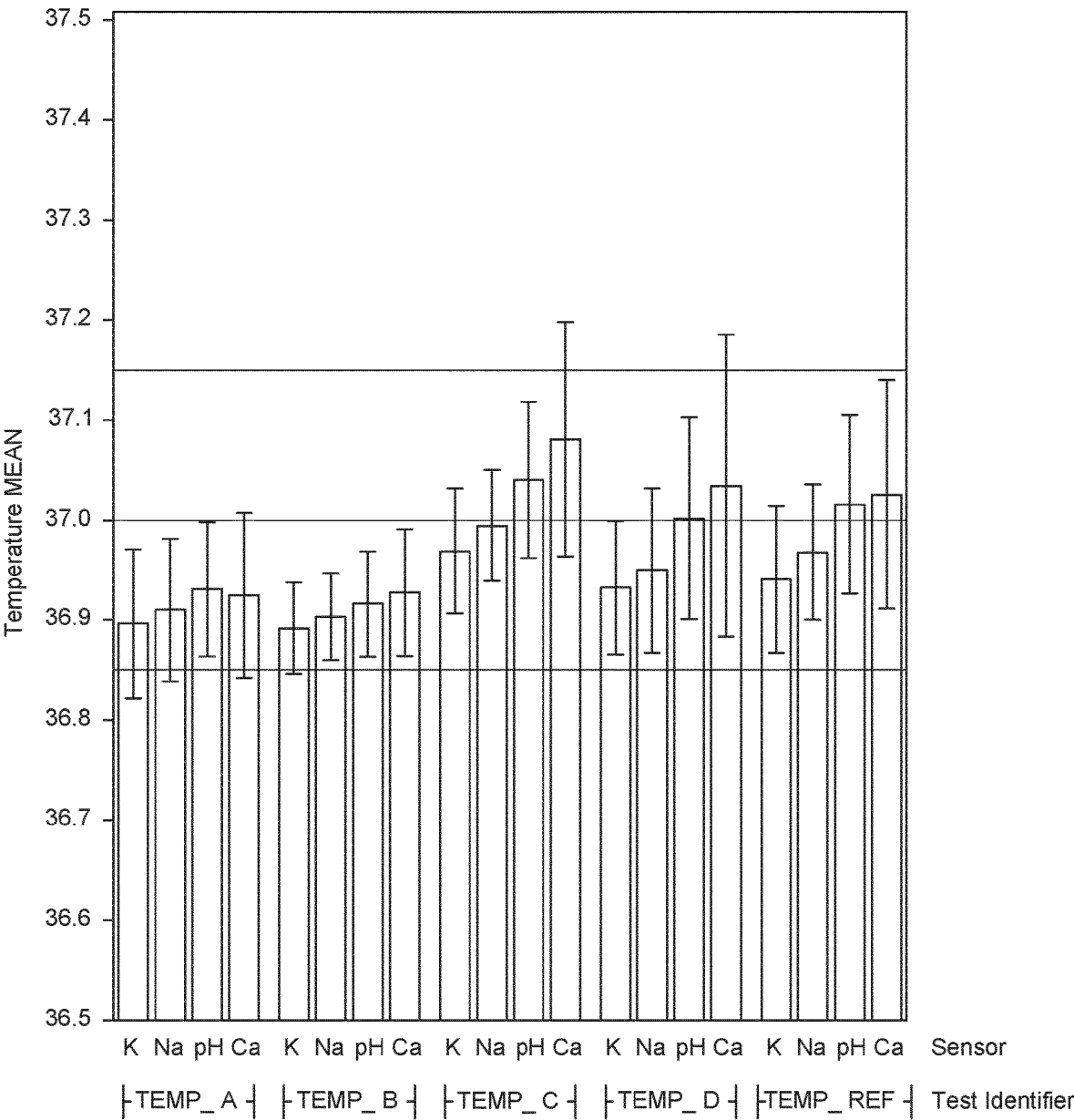
Figure 11:
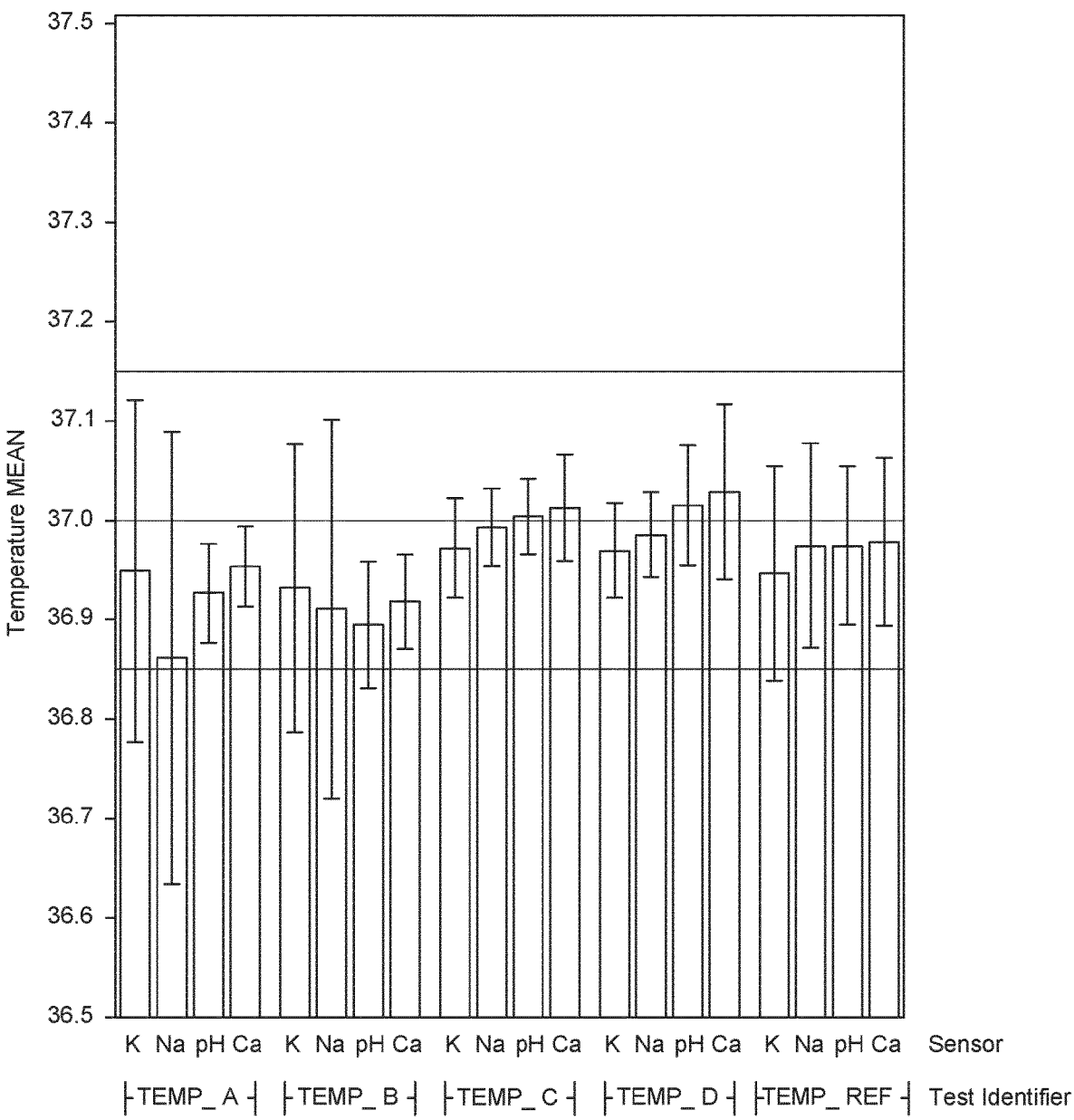
Figure 12:
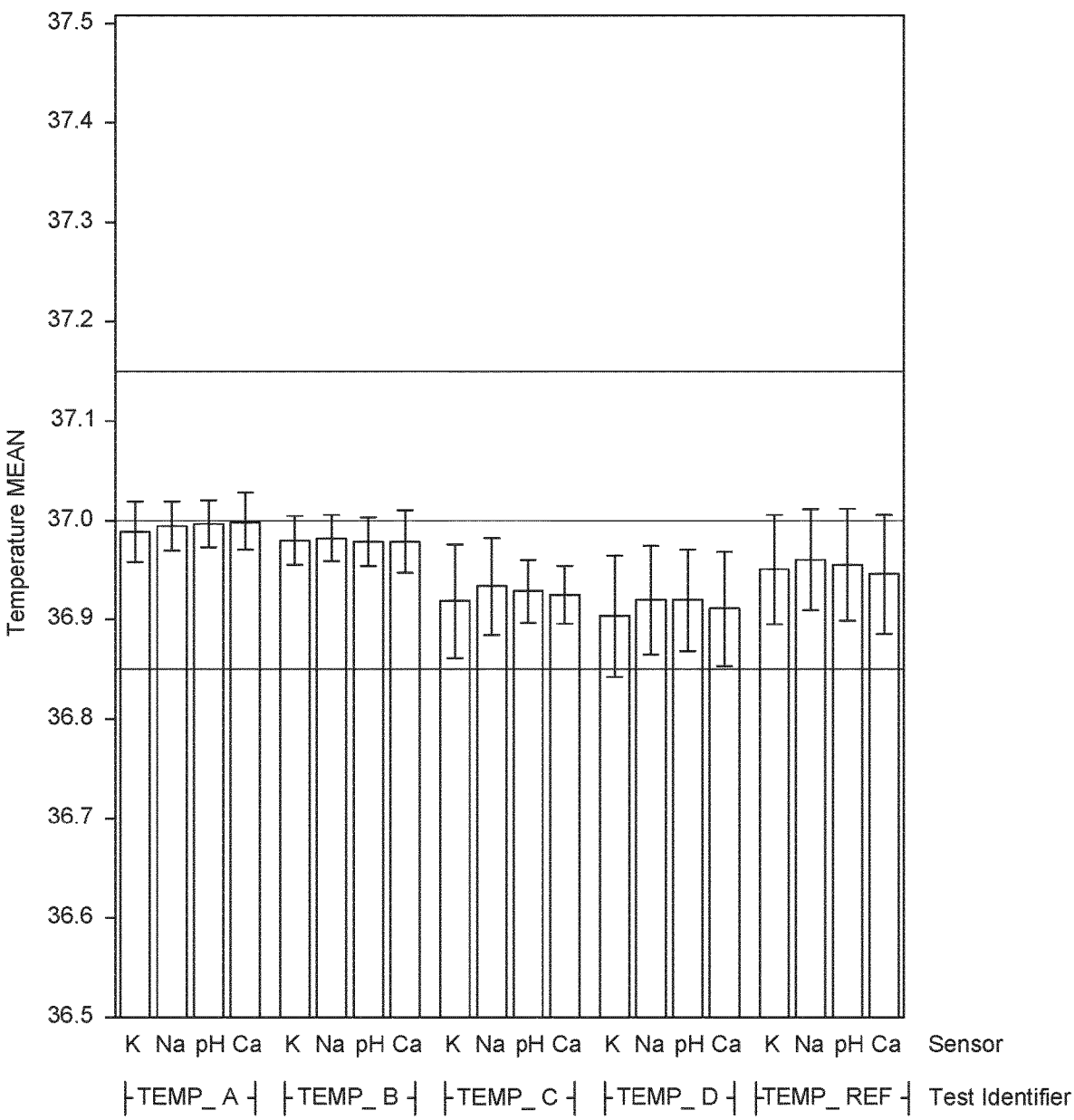

| FIG. No. | Lab Temperature | Sample Temperature |
|---|---|---|
| FIG. 7 | 15° C. | 0° C. |
| FIG. 8 | 25° C. | 0° C. |
| FIG. 9 | 32° C. | 0° C. |
| FIG. 10 | 15° C. | 15° C. |
| FIG. 11 | 25° C. | 25° C. |
| FIG. 12 | 32° C. | 32° C. |

Based on the above experimental data, while all examples A-D having only a heating element disposed at the first wall provide acceptable results, even when compared to existing relatively complicated measurement chamber designs with heating traces on both of the first and second walls of the measurement chamber, heater trace layout B appears to be preferred because:

The performance results are comparable to relatively complicated existing measurement chamber designs with heater lanes on both of the first and second walls of the chamber.

The temperature uniformity across the measurement chamber is preferred compared to the other tested examples (i.e. examples A, C and D).

Although the invention has been described with reference to certain specific embodiments, various modifications thereof will be apparent to those skilled in the art without departing from the spirit and scope of the invention as outlined in claims appended hereto.

In particular, some embodiments have mainly been described with reference to a particular type of measurement chamber. It will be appreciated, however, that other embodiments of a sensor device include other types of measurement chambers. Accordingly, the various embodiments of a heating element or system of heating elements described herein that are configured to heat the fluid accommodated within a measurement chamber, wherein the heating element is configured to provide a larger heating effect in a proximity of the inlet of the measurement chamber than in a proximity of the outlet of the measurement chamber, may be included in a variety of different types of sensor devices, in particular sensor devices having different types of measurement chambers.

Generally, in some embodiments, a heating element as described herein is included in a sensor device comprising: a) a first electronic wiring substrate having a first and a second surface and at least one analyte sensor formed on the first surface thereof, the at least one analyte sensor being connected with one or more electrical contact points, b) a second electronic wiring substrate having a first and a second surface and at least one analyte sensor formed on the first surface part thereof, the at least one analyte sensor being connected with one or more electrical contact points, and c) a spacer having a through-going recess with a first and a second opening, wherein the first substrate, the second substrate and the spacer are arranged in a layered structure, where the first surface of the first substrate closes the first opening of the spacer and the first surface of the second substrate closes the second opening of the spacer, thereby forming a measuring chamber which is faced by at least one analyte sensor from each of the substrates. Such sensor devices have been described in WO2008/131767 (Radiometer Medical ApS). In a further embodiment hereof, the volume of the measuring chamber is less than 1 ml, such as less than 0.5 ml, e.g. less than 200 microliter, such as less than 100 microliter, e.g. less than 50 microliter, such as less than 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48 or 49 microliter. In a further embodiment, the volume of the measuring chamber is between 2 and 50 microliter, e.g. from 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48 or 49 microliter to 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 microliter. Thus, in one embodiment, the volume used for the determination, i.e. the volume contained within the measuring chamber, is less than 1 ml, such as less than 0.5 ml, e.g. less than 200 microliter, such as less than 100 microliter, e.g. less than 50 microliter, such as between 2 and 50 microliter, e.g. from 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48 or 49 microliter to 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 microliter. The measuring chamber provided by the recess in the spacer and the first surfaces of the first and second substrates preferably provides a volume of about 25-45 microliter, more preferably a volume of about 30-40 microliter. With such a volume very small samples are required for measurement by the analyte sensors in the measuring chamber. Preferably the dimensions of the spacer are within the ranges: length 20-60 mm, width 5-20 mm, and thickness 0.2-0.6 mm. The recess within the spacer may have the dimensions within the ranges: length 10-50 mm, width 1-5 mm, and depth 0.2-0.6 mm. The dimensions of the first and second substrates and the spacer, and thus, the dimension of the sensor device may be adapted depending on the intended use. However, in a preferred embodiment the first substrate has dimensions within the ranges: length about 20-60 mm, width about 5-20 mm, and thickness about 0.3-0.8 mm. The width and/or the length of the second substrate may be somewhat larger than the width and/or length of the first substrate. This is due to the fact that for some preferred embodiments it is preferred that the first surface of the second substrate projects over the edges of the spacer and first substrate in the sensor device. The second substrate preferably has dimensions within the ranges: length about 20-60 mm, width about 5-40 mm, and thickness 0.3-0.8 mm. The length and width of the second substrate may provide an extension beyond the edges of the first substrate and spacer in the range of about 4-20 mm.

In another embodiment, the heating element described herein is included in a sensor device comprising: a housing having a base, a top spaced above the base, and an outer wall that extends from the base to the top; an inlet in the housing that is sized to receive a sample of the fluid; a plurality of partitions arranged around the fluid inlet and substantially isolated from each other, each partition having a port at the fluid inlet for receiving a portion of the sample of fluid received by the fluid inlet; and at least one sensor in each partition, wherein the at least one sensor is responsive to the fluid when the fluid contacts the at least one sensor, wherein the sensor device is configured to selectively direct the sample of fluid received by the one or more of the plurality of partitions from the fluid inlet into contact with the at least one sensor. Such sensor devices have been described in WO 2018/112017. In a further embodiment hereof, the volume used for the determination in each partition, i.e. the volume contained within the partition, is less than 1 ml, such as less than 0.5 ml, e.g. less than 200 microliter, such as less than 100 microliter, e.g. less than 50 microliter, such as between 2 and 50 microliter, e.g. from 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48 or 49 microliter to 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 microliter.

In another embodiment, the heating element described herein is included in a sensor device comprising: a first microsensor having a first outer sheath, a first membrane core within the first outer sheath, and a first conductive element that is at least partially encased by and in contact with the first membrane core, wherein the first conductive element detects a first electrical response signal when the first membrane core is in contact with a fluid; and a second microsensor adjacent to the outer surface of the first microsensor, the second microsensor having a second outer sheath, a second membrane core within the second outer sheath, and a second conductive element that is at least partially encased by and in contact with the second membrane core, wherein the second conductive element detects a second electrical response signal when the second membrane core is in contact with the fluid. Such sensor devices have been described in WO 2018/112012. In a further embodiment hereof, the volume used for the determination, i.e. the volume contained within the measuring chamber, is less than 1 ml, such as less than 0.5 ml, e.g. less than 200 microliter, such as less than 100 microliter, e.g. less than 50 microliter, such as between 2 and 50 microliter, e.g. from 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48 or 49 microliter to 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 microliter.

In another embodiment, the heating element described herein is included in a microcapillary sensor device, comprising: a sensor body elongated along a longitudinal axis, the sensor body having a first end, a second end spaced from the first end along the longitudinal axis, an outer surface, and an inner surface, wherein the inner surface defines a hollow capillary that extends from the first end toward the second end along the longitudinal axis; a sensing element that extends through the sensor body from the outer surface to the hollow capillary; and a conductive element in contact with the sensing element; wherein the conductive element detects a response signal generated by a reaction between the sensing element and a fluid as the fluid flows through the hollow capillary contacting the sensing element. Such sensor devices have been described in WO 2018/112008. In a further embodiment hereof, the volume used for the determination, i.e. the volume contained within the measuring chamber, is less than 1 ml, such as less than 0.5 ml, e.g. less than 200 microliter, such as less than 100 microliter, e.g. less than 50 microliter, such as between 2 and 50 microliter, e.g. from 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48 or 49 microliter to 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 microliter.

In another embodiment, the heating element described herein is included in a sensor device comprising: a first planar substrate with a first planar surface; a second planar substrate with a second planar surface; a first sensing area and a second sensing area, the first sensing area and the second sensing area being disposed in between the first planar surface and the second planar surface, both of the first sensing area and the second sensing area comprising a chemical and/or reagent in electrical connection with a first electrode and a second electrode, respectively; a first planar intermediate isolating layer with a flow channel, wherein the first sensing area opposes the second sensing area with the flow channel disposed in between the first sensing area and the second sensing area; and a first heating element disposed in between the first planar surface and the second planar surface. Such sensor devices have been described in WO 2017/120464. In a further embodiment hereof, the volume used for the determination, i.e. the volume contained within the measuring chamber, is less than 1 ml, such as less than 0.5 ml, e.g. less than 200 microliter, such as less than 100 microliter, e.g. less than 50 microliter, such as between 2 and 50 microliter, e.g. from 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48 or 49 microliter to 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 microliter.

In another embodiment, the heating element described herein is included in a sensor device comprising: a first planar intermediate isolating layer with at least a first sensing area; a second planar intermediate isolating layer with at least a second sensing area; a third planar intermediate isolating layer with a flow channel 14, wherein the first sensing area opposes the second sensing area with the flow channel disposed in between the first sensing area and the second sensing area; a first planar conductive layer disposed adjacent to the first intermediate isolating layer opposite the third planar intermediate isolating layer; a first planar substrate disposed adjacent to the first planar conductive layer opposite the first intermediate isolating layer; a second planar substrate disposed adjacent to the second planar intermediate isolating layer opposite the third planar intermediate isolating layer, the second planar substrate having at least a first conductive via in electrical contact with the second sensing area; and a second planar conductive layer disposed adjacent to the second planar substrate opposite the second planar intermediate isolating layer, the second planar conductive layer being in electrical contact with first conductive via, wherein each of the first planar intermediate isolating layer, the second planar intermediate isolating layer, the third planar intermediate isolating layer, first planar conductive layer, the first planar substrate, the second planar substrate, and the second planar conductive layer have two planar surfaces separated by a thickness, each of the respective two planar surface having an planar area that is approximately equal, wherein the planar area of first conductive layer is greater than the planar area of each of the first planar intermediate isolating layer, the second planar intermediate isolating layer, the third planar intermediate isolating layer, the second planar substrate, and the second planar conductive layer. Such sensor devices have been described in WO 2017/019609. In a further embodiment hereof, the volume used for the determination, i.e. the volume contained within the measuring chamber, is less than 1 ml, such as less than 0.5 ml, e.g. less than 200 microliter, such as less than 100 microliter, e.g. less than 50 microliter, such as between 2 and 50 microliter, e.g. from 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48 or 49 microliter to 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 microliter.

In another embodiment, the heating element described herein is included in a sensor device comprising: a single substrate, the substrate having a first surface, the first surface having a first area and a second area separated by a line, the first area opposing the second area of the first surface of the single substrate; a conductor layer disposed on the single substrate, the conductor layer comprising a first group of electrodes printed in the first area and a second group of electrodes printed in the second area; a dielectric layer disposed on the conductor layer, the dielectric layer comprising a first area of dielectric material disposed on the first group of electrodes and a second area of dielectric material disposed on the second group of electrodes, the first area of dielectric material and the second area of dielectric material each comprising a respective first group and a second group of reaction wells formed in the dielectric layer, at least one reaction well being electrically coupled to a respective electrode and containing chemistries; and a spacer layer adjacent to the first area of dielectric material and the second area of dielectric material, the spacer layer forming a flow path between the first group and the second group of reaction wells. Such sensor devices have been described in WO 2016/106320. In a further embodiment hereof, the volume used for the determination, i.e. the volume contained within the measuring chamber, is less than 1 ml, such as less than 0.5 ml, e.g. less than 200 microliter, such as less than 100 microliter, e.g. less than 50 microliter, such as between 2 and 50 microliter, e.g. from 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48 or 49 microliter to 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 microliter.

In another embodiment, the heating element described herein is included in a test strip comprising: a first planar substrate with coplanar electrodes on a first planar surface and a second planar substrate with coplanar electrodes on a second planar surface, the first planar substrate and the second planar substrate being arranged such that the first surface of the first planar substrate opposes the second planar surface of the second planar substrate; an intermediate layer disposed in between the opposed first surface of the first planar substrate and the second planar surface of the second planar substrate; the first planar surface of the first planar substrate having a first sensing area electrically connected to a first electrical contact; and the second planar surface of the second planar substrate having a second electrical contact electrically connected to the first electrical contact via a conductive element, the conductive element extending between the first surface of the first planar substrate and the second surface of the second planar substrate without passing through the first planar substrate or the second planar substrate. Such test strips have been described in WO 2016/011308 In a further embodiment hereof, the volume used for the determination, i.e. the volume contained within the measuring chamber, is less than 1 ml, such as less than 0.5 ml, e.g. less than 200 microliter, such as less than 100 microliter, e.g. less than 50 microliter, such as between 2 and 50 microliter, e.g. from 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48 or 49 microliter to 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 microliter.

In another embodiment, the heating element described herein is included in a sensor device comprising: a first planar substrate having a base layer, a conductive layer formed on a first planar surface of the base layer, and an dielectric layer formed on at least one of a first planar surface of the conductive layer or the first planar surface of the base layer, the dielectric layer having a first planar surface located a distance from the first planar surface of the conductive layer, the conductive layer comprising at least at least a first electrical contact and a second electrical contact electrically isolated from the first electrical contact, the dielectric layer defining a liquid flow path through the dielectric layer, the flow path having two side walls and a bottom surface extending between the two side walls, the two side walls extending between the first planar surface of the base layer and the first planar surface of the dielectric layer, and the dielectric layer further defining a first sensing area and a second sensing area above the respective first electrical contact and the second electrical contact of the conductive layer, the first sensing area and the second sensing area allowing liquid in the flow path to contact the first electrical contact and the second electrical contact, respectively; and a second planar substrate, the second substrate being bonded to the first substrate, when bonded to the first substrate the second substrate defining a upper surface of the liquid flow path, the upper surface of the liquid flow path extending between the two side walls and located at a distance from the bottom surface of the flow path. Such sensor devices have been described in WO 2016/007716. In a further embodiment hereof, the volume used for the determination, i.e. the volume contained within the measuring chamber, is less than 1 ml, such as less than 0.5 ml, e.g. less than 200 microliter, such as less than 100 microliter, e.g. less than 50 microliter, such as between 2 and 50 microliter, e.g. from 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48 or 49 microliter to 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 microliter.

In another embodiment, the heating element described herein is included in a sensor device, comprising: a substrate having a first surface and a second surface opposite the first surface; at least one analyte sensor positioned on at least one of the first surface and the second surface of the substrate; and at least one electrical contact positioned on the substrate in electrical communication with a corresponding one of the at least one analyte sensor, wherein the substrate is configured to define a tube having an interior surface, and an exterior surface with at least a portion of the first surface of the substrate defining the interior surface of the tube and the at least one analyte sensor disposed on at least one of the interior surface and the exterior surface of the tube. Such sensor devices have been described in WO 2013/163120. In a further embodiment hereof, the volume used for the determination, i.e. the volume contained within the measuring chamber, is less than 1 ml, such as less than 0.5 ml, e.g. less than 200 microliter, such as less than 100 microliter, e.g. less than 50 microliter, such as between 2 and 50 microliter, e.g. from 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48 or 49 microliter to 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 microliter.

The invention claimed is:

1. A sensor device, comprising:

a measurement chamber having at least a first wall, the measurement chamber including a plurality of analyte sensors; wherein the measurement chamber allows a fluid to be analyzed to interact with each of the plurality of analyte sensors when the fluid is accommodated within the measurement chamber; the measurement chamber having an inlet configured to receive the fluid to be analyzed and an outlet configured to allow the fluid to exit the measurement chamber after having interacted with the plurality of analyte sensors; the measurement chamber defining a sample volume for accommodating the fluid to be analyzed, the sample volume extending at least between the inlet and the outlet; and a heating element including a first portion and a second portion, the heating element being configured to heat the fluid accommodated within the measurement chamber, the first portion being closer to the inlet of the measurement chamber than the second portion, wherein the first portion comprises a larger trace density than the second portion to provide a larger heating effect along the first portion than along the second portion.

2. The sensor device according to claim 1; comprising at least a second wall of the measurement chamber opposite the first wall.

3. The sensor device according to claim 2; wherein the first wall has a first surface facing the second wall, and a second surface, opposite the first surface and facing away from the second wall; wherein the heating element is disposed at the second surface of the first wall.

4. The sensor device according to claim 1; wherein the heating element is disposed only on the first wall.

5. The sensor device according to claim 1, wherein the heating element comprises a heating trace made from an electrically conductive material disposed at a surface of the first wall and extending between a first end point and a second end point.

6. The sensor device according to claim 5; wherein the heating trace is disposed in a meandering and/or serpentine and/or helical layout.

7. The sensor device according to claim 5; wherein the heating trace is disposed in a heating trace layout, the heating trace layout defining a trace density as a length of heating trace per unit surface area; wherein the trace density is higher in a proximity of the inlet than in a proximity if the outlet.

8. The sensor device according to claim 7; wherein the measurement chamber defines a flow path between the inlet and the outlet of the measurement chamber; wherein the trace density is higher along a first portion of the measurement chamber between the inlet and a reference position along the flow path than along a second portion of the measurement chamber extending between the reference position and the outlet.

9. The sensor device according to claim 5; wherein the heating trace has an electric resistivity that varies along the heating trace.

10. The sensor device according to claim 1; comprising a first substrate layer defining the first wall of the measurement chamber.

11. The sensor device according to claim 10; wherein the first substrate layer comprises a central layer portion and a peripheral layer portion, the central layer portion defining the first wall of the measurement chamber and the peripheral layer portion being laterally displaced from the measurement chamber; wherein the measurement chamber defines a flow path defined between the inlet and the outlet of the measurement chamber; and wherein the heating trace comprises a peripheral trace portion and a central trace portion, the peripheral trace portion being disposed on a surface of the peripheral layer portion and the central trace portion being disposed on the central layer portion.

12. The sensor device according to claim 11; wherein the peripheral trace portion is substantially uniformly distributed along a length of the flow path between the inlet and the outlet.

13. The sensor device according to claim 11; wherein the central trace portion is non-uniformly distributed along a length of the flow path between the inlet and the outlet, such that a trace density of the central trace portion is higher in a proximity of the inlet than in a proximity if the outlet.

14. The sensor device according to claim 13; wherein the central trace portion is only disposed in a portion of the measurement chamber proximal to the inlet.

15. The sensor device according to claim 10, wherein the sensor device comprises at least a second wall of the measurement chamber opposite the first wall and a second substrate layer defining the second wall of the measurement chamber.

16. The sensor device according to claim 15, comprising an intermediate layer disposed between the first and second substrate layers, the intermediate layer accommodating the measurement chamber.

17. The sensor device according to claim 15, wherein each of the inlet and outlet extend through the first substrate layer or the second substrate layer.

18. The sensor device according to claim 1; comprising a temperature sensor.

19. The sensor device according to claim 18; wherein the temperature sensor is disposed at a surface of the first wall at a location without heating traces.

20. The sensor device according to claim 18, wherein the temperature sensor is disposed at a central portion of the measurement chamber.

21. The sensor device according to claim 1, comprising only a single heating element.

22. The sensor device according to claim 1, wherein each of the analyte sensors is configured to sense a parameter of one or more analytes selected from:

$pO_2$, $pCO_2$, and pH;

concentrations of electrolytes;

concentrations of metabolic factors; and concentrations of enzymes.

23. The sensor device according to claim 1, configured for analyzing parameters of liquid samples.

24. The sensor device according to claim 1, wherein the fluid is a liquid selected from: blood, diluted or undiluted whole blood, serum, plasma, saliva, urine, cerebrospinal liquid, pleura, synovial liquid, ascites liquid, peritoneal liquid, amniotic liquid, milk, and dialysis liquid samples.

25. The sensor device according to claim 1, wherein the heating element is positioned closer to the outlet than to the inlet of the measurement chamber.

26. An analyzer apparatus comprising a sensor device retaining mechanism configured to receive a sensor device according to claim 1.

27. The analyzer apparatus according to claim 26; wherein the sensor device retaining mechanism comprises:

a preheating element configured to pre-heat fluid flowing towards the inlet of the sensor device.

28. A method, the method comprising using the heating element of claim 1 to provide a larger heating effect via the first portion, nearer the inlet of the measurement chamber, than via the second portion, nearer outlet of the measurement chamber.

* * * * *